(12) United States Patent
Gilbert et al.

(10) Patent No.: US 8,282,614 B2
(45) Date of Patent: Oct. 9, 2012

(54) METHOD AND APPARATUS FOR PRODUCING STABILIZED ABSORBENT STRUCTURE

(75) Inventors: Steven Ray Gilbert, Fairfield, OH (US); Jeffrey Scott Hudson, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 1464 days.

(21) Appl. No.: 11/601,946

(22) Filed: Nov. 20, 2006

(65) Prior Publication Data
US 2008/0119811 A1 May 22, 2008

(51) Int. Cl.
*A61F 13/15* (2006.01)
*A61F 13/20* (2006.01)

(52) U.S. Cl. .................................... 604/385.18
(58) Field of Classification Search .............. 604/385.19
See application file for complete search history.

(56) References Cited

U.S. PATENT DOCUMENTS

| | | | | |
|---|---|---|---|---|
| 2,926,394 | A * | 3/1960 | Bletzinger et al. ........... | 28/120 |
| 5,004,579 | A | 4/1991 | Wislinski et al. | |
| 5,153,971 | A | 10/1992 | Van Iten | |
| 6,003,216 | A | 12/1999 | Hull, Jr. et al. | |
| 6,299,573 | B1 | 10/2001 | Hull, Jr. et al. | |
| 6,682,513 | B2 | 1/2004 | Agyapong et al. | |
| 7,047,608 | B2 | 5/2006 | Sageser et al. | |
| 7,120,977 | B2 | 10/2006 | Bittner et al. | |
| 7,124,483 | B2 | 10/2006 | Prosise et al. | |
| 2004/0226152 | A1 | 11/2004 | Prosise et al. | |
| 2006/0105075 | A1 | 5/2006 | Otsubo | |

FOREIGN PATENT DOCUMENTS

| | | | |
|---|---|---|---|
| EP | 0 260 932 A2 | | 3/1988 |
| EP | 1666010 A1 | * | 6/2006 |
| WO | WO 98/43589 | * | 10/1998 |
| WO | WO 03/079949 | * | 10/2003 |
| WO | WO 2004/100847 A1 | * | 11/2004 |

OTHER PUBLICATIONS

PCT International Search Report dated Apr. 23, 2008.
U.S. Appl. No. 11/595,322, filed Nov. 10, 2006, Gilbert et al.

* cited by examiner

*Primary Examiner* — Tatyana Zalukaeva
*Assistant Examiner* — Ginger T Chapman
(74) *Attorney, Agent, or Firm* — Andres E. Velarde; James Oehlenschalger

(57) ABSTRACT

A process and apparatus for producing a stabilized product from a pledget, including the steps of providing a pledget and a transfer member, and pushing the compressed pledget into a stabilization mold with the transfer member as the transfer member advances to a loading position. The transfer member is retracted to a stabilizing position. The compressed pledget is stabilized while the compressed pledget is maintained in compression by the transfer member and the stabilization mold to form a stabilized tampon.

14 Claims, 17 Drawing Sheets

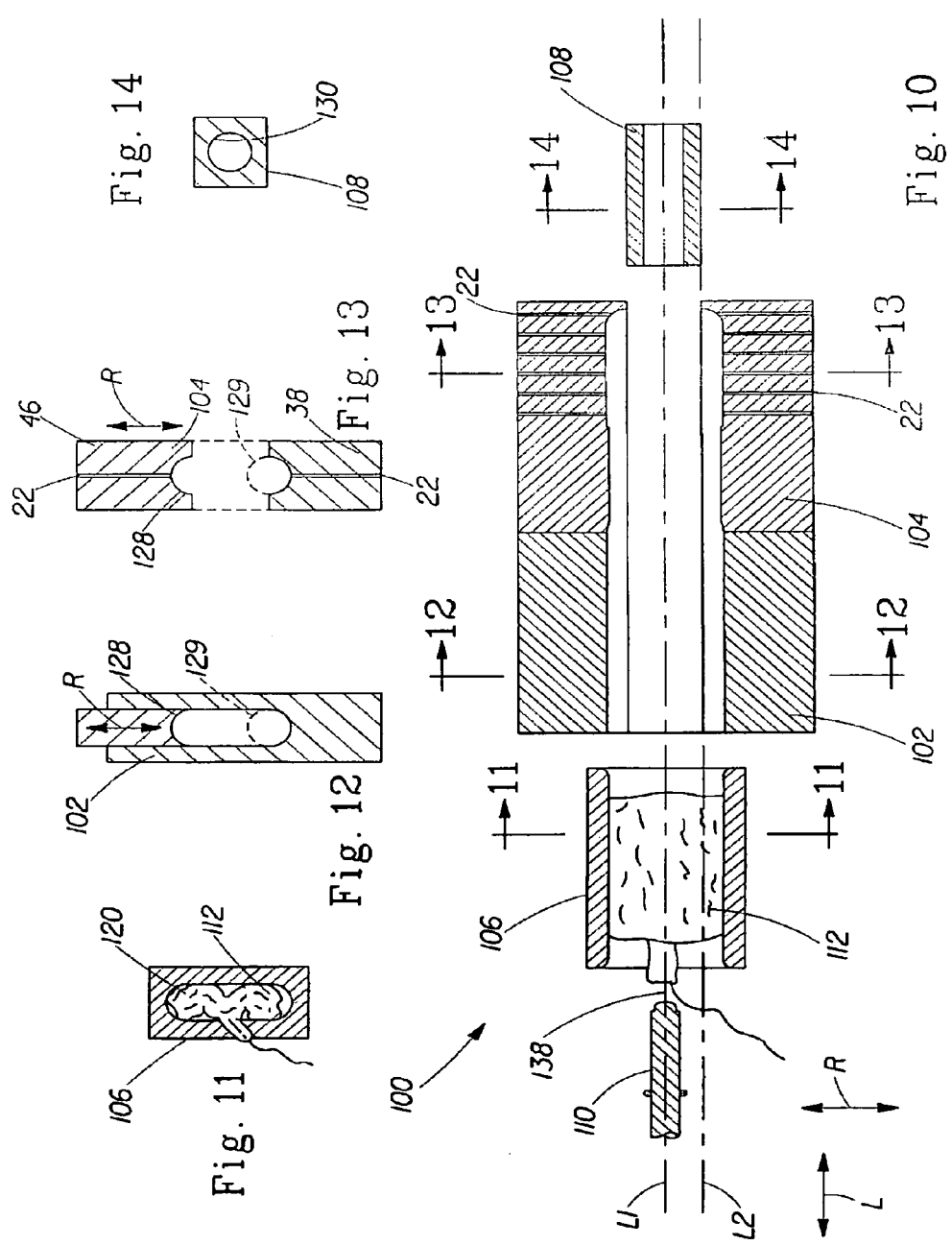

ate of absorbent material prior to compression or subsequent to the expansion of the material.

METHOD AND APPARATUS FOR PRODUCING STABILIZED ABSORBENT STRUCTURE

BACKGROUND OF THE INVENTION

During the production of compressed products from pledgets, it is often required to form the product under sustained high pressure, while exposing the pledget to thermal molding conditions. However, certain characteristics of the compressed products such as expansion properties and/or aesthetics can be affected by such high degrees of molding force and thermal treatments. Thus, known manufacturing processes may compromise between certain performance characteristics that can be achieved in the products, or portions thereof.

Therefore, a technique that is capable of providing a stable product, with improved properties, such as, for example, higher degrees of expansion may be desirable. Further, a technique that provides a stable product with a high surface finish quality may also be desirable.

BRIEF SUMMARY OF THE INVENTION

The invention relates to a process and apparatus for producing a stabilized product from a pledget, including the steps of providing a pledget and a transfer member, and compressing the compressed pledget into a stabilization mold with the transfer member as the transfer member advances to a loading position. The transfer member is retracted to a stabilizing position. The pledget is stabilized, to form a stabilized product. The pledget is maintained in compression by the transfer member and the stabilization mold during the step of stabilizing the pledget.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying Figures, in which:

FIG. 10 is a cross-sectional view of one embodiment of the process of the present invention.

FIG. 11 is a cross-sectional view of a pledget infeed carrier of FIG. 10, taken along line 11-11.

FIG. 12 is a cross-sectional view of the split compression mold of FIG. 10, taken along line 12-12.

FIG. 13 is a cross-sectional view of the split stabilization mold of FIG. 10, taken along line 13-13.

FIG. 14 is a cross-sectional view of a tampon discharge carrier of FIG. 10, taken along line 14-14.

DETAILED DESCRIPTION OF THE INVENTION

Figure 1:
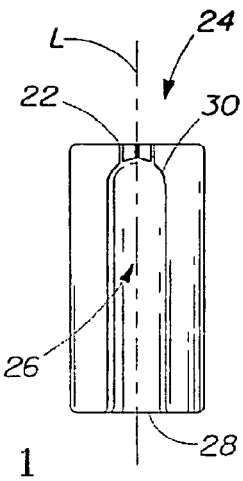
FIG. 1. is a cross-section of a unitary embodiment of a permeable mold with pores located axially along the mold.

As used herein, the term "pledget" refers to a construction of absorbent material prior to the compression of such construction into a tampon or other absorbent product. The pledget and compressed product may be a tampon, including nosepacks, a tampon used to absorb menses or other feminine hygiene products, incontinence articles, bandages, or any other compressed absorbent product. Where the term "tampon" is used herein, that usage is for illustrative purposes only, and is not to be construed as limiting.

As used herein, "compression" refers to the process of pressing, squeezing, compacting, or otherwise manipulating the size, shape, and/or volume of a material to obtain a compressed pledget having a suitable shape. Where the product is a compressed tampon pledget, the shape may be a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

As used herein, "mold" refers to a structure for shaping a pledget during compression and/or retaining the shape for a compressed pledget subsequent to compression during the stabilization process. Molds have an inner surface defining an inner cavity and an outer surface. The inner cavity is generally structured to define or mirror the shape of the product being formed. Thus, in some embodiments the pledget conforms to the shape of the inner cavity of the mold by a restraining force to result in a self-sustaining shape, and is retained in the inner cavity during the stabilization process. In other embodiments, the mold retains the shape of the compressed pledget during the stabilization process. The inner cavity may be profiled to achieve any shape known in the art including, but not limited to, cylindrical, rectangular, triangular, trapezoidal, semi-circular, hourglass, serpentine, or other suitable shapes. The outer surface of the mold is the surface external to the inner surface and can be profiled or shaped in any manner, such as rectangular, cylindrical, or oblong. The mold may comprise one or more members. One mold used in the present invention may be a unitary mold, comprising one member, as shown for example, in FIGS. 1 and 2, or a "split cavity mold," as shown for example, in FIG. 3, FIG. 4, FIG. 5, FIG. 6, and FIG. 7. Split cavity molds are generally used when producing shaped tampons, such as those disclosed in U.S. Pat. Nos. 6,824,536 and 6,932,805. Unitary molds are typically used for less complex shapes such as cylindrical or substantial cylindrical.

The term "permeable," as used herein, refers to the ability of a material to allow the spread or infusion of a gas, a liquid, or a evaporative material through the material's composition. It is to be understood that "gas," as used in this document, refers to any suitable substance, including those in gaseous, liquid, or evaporative forms. A material may be permeable due to its composition or the material may be fabricated from impermeable material then modified to become permeable, either chemically, mechanically, or electrically, such as, for example, by acid etching, drilling, or aperturing.

The term "pores," as used herein, refers to small openings or interstices that connect the inner surface of the mold with the outer surface of the mold, admitting the passage and infusion of gases into and through a compressed tampon pledget contained within the inner cavity of the mold.

As used herein, "self-sustaining" is a measure of the degree or sufficiency to which an absorbent material, such as a tampon or other absorbent product, retains its compressed form after stabilization, such that, in the absence of external forces, the resulting product will tend to retain its shape and size. For tampons, it is found that control of the level of moisture within the tampon is a factor for helping the tampon to retain its vaginally insertable shape and size subsequent the absence of the external compression forces. This self-sustaining form need not persist during actual use of the tampon. That is, once the tampon is inserted into the vagina or other body cavity and begins to acquire fluid, the tampon may expand and lose its self-sustaining form.

The term "shaped tampons," as used herein, refers to compressed tampon pledgets having either a substantially serpentine shape, or an "undercut" or "waist." The phrase "substantially serpentine" refers to a non-linear dimension between any two points spaced at least about 5 mm apart. The term "undercut" refers to tampons having a protuberance or indentation that impedes the withdrawal from a unitary mold. For example, shaped tampons may be hourglass shaped having at least one perimeter in the center of the tampon or "waist" that is less than both an insertion end perimeter and a withdrawal end perimeter.

As used herein, the term "split cavity mold" is a mold comprised of two or more members that, when brought together, complete the inner cavity of the mold. Each member of the split cavity mold comprises at least a portion of the inner surface that when brought together or closed completes the mold structure. The split cavity mold is designed such that at least two or more of the mold members can be at least partially separated, if not fully separated, typically after the tampon has acquired a self-sustaining shape, to expand the cavity volume circumscribed by the inner surface(s), thus permitting the easier removal of the tampon from the mold. Where each member's inner surface portion joins the inner surface portion of another member, those points of adjacency can define a straight line, a curve, or another seam of any convoluted intersection or seam of any regular or irregular form. The elements of the split cavity in some embodiments may be held in appropriate position relative to each other by linking elements of any form including bars, rods, linked cams, chains, cables, wires, wedges, screws, etc.

The term "stabilized," as used herein, refers to a product in a self-sustaining state, wherein it has overcome the natural tendency to re-expand to the original size, shape, and volume of the absorbent material and overwrap, which comprise the pledget.

As used herein, the terms "tampon" or "stabilized tampon" refer to any type of absorbent structure that is inserted into the vaginal canal or other body cavities for the absorption of fluid therefrom, to aid in wound healing, or for the delivery of active materials, such as medicaments, or moisture. Other absorbent products may also be formed and stabilized through the processes described herein, including without limitation, sanitary napkins, wipes, cleaning products, diapers, makeup applicators, makeup removers, sponges, and other products that expand. The tampon, or other absorbent product, may be compressed into a generally cylindrical configuration in the radial direction, axially along the longitudinal axis, or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis, and a radial axis. The tampon's length can be measured from the insertion end to the withdrawal end along the longitudinal axis. A typical tampon for human use is about 30 to about 60 mm in length. A tampon may be straight or non-linear in shape, such as curved along the longitudinal axis. A typical tampon is about 8 to about 20 mm wide. The width of a tampon, unless otherwise stated in the specification, corresponds to the length across the largest cylindrical cross-section, along the length of the tampon.

The term "vaginal cavity," "within the vagina," and "vaginal interior," as used herein, are intended to be synonymous, and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring) and the cervix. The terms "vaginal cavity," "within the vagina," and "vaginal interior" do not include the interlabial space, the floor of vestibule, or the externally visible genitalia.

As used herein, "cm" is centimeter, "g" is grams, "g/m$^2$" is grams per meter squared, "l" is liters, "l/s" is liters per second, "ml" is milliliters", "mm" is millimeters, "min" is minutes, "rpm" rate per minute, and "s" is seconds.

Figure 2:
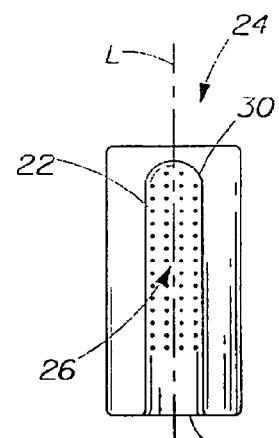
FIG. 2 is a cross-section of a unitary embodiment of a permeable mold with pores located radially along the mold.

FIG. 1 and FIG. 2 show cross sections of a unitary embodiment of a permeable mold with a longitudinal axis L. The structure of the unitary mold 24 is a one piece mold so arranged as to define a space or inner cavity 26 for shaping a pledget during compression and/or retaining the shape for a compressed pledget subsequent to compression during the stabilization process. The inner cavity 26 has an open proximal end 28 and a closed distal end 30. In the unitary embodiments of the permeable mold, the open proximal end 28 may be used for both an ingress port where the pledget is introduced into the inner cavity 26 and an egress port where the final compressed product can be extracted from the inner cavity 26. In the embodiment shown in FIG. 1, the unitary mold 24 has pores 22 located axially along the unitary mold 24, the pores 22 being shown at the closed distal end 30. As shown in FIG. 2, the unitary mold 24 has pores 22 located radially along the unitary mold 24.

Figure 3:
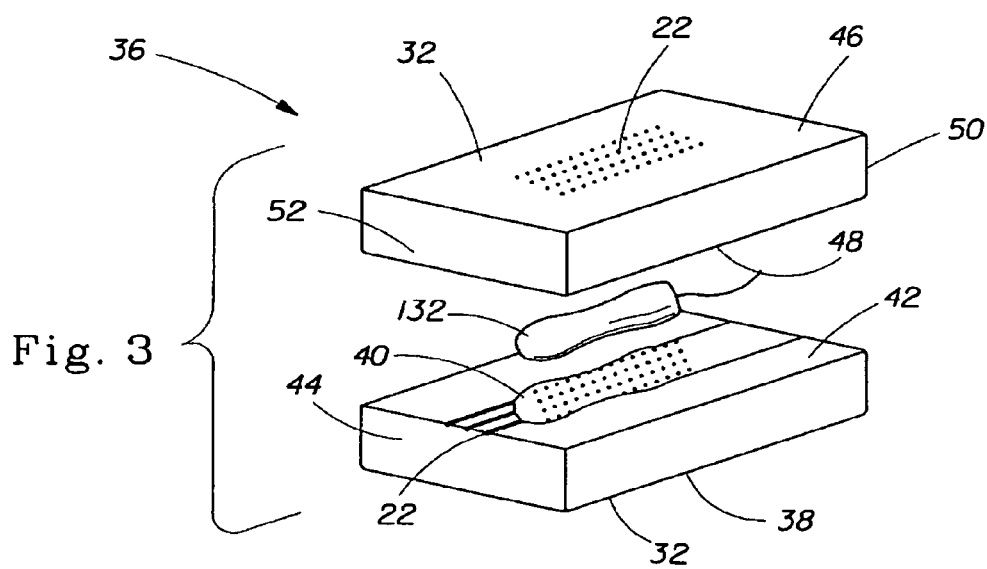
FIG. 3 is an exploded view of a split cavity mold with the compressed tampon pledget positioned between the first split cavity mold member and the second split cavity mold member.

FIG. 3 shows an exploded view of an example of a split cavity mold 36 with a compressed pledget 132 positioned between first split cavity mold member 38 and second split cavity mold member 46. The first split cavity mold member 38 and second split cavity mold member 46 are combined to form a split cavity mold 36. The first split cavity mold member 38 has a first inner surface 40 and an outer mold surface 32. The second split cavity mold member 46 is substantially similar, if not a mirror image or not identical in size, shape, and dimension, to the first split cavity mold member 28, and has a second inner surface 48 and an outer mold surface 32. The first split cavity mold member 38 and the second split cavity mold member 46 are configured such that the first end 42 and the second end 44 of the first split cavity mold member 38 corresponds to the first end 50 and the second end 52 of the second split-cavity mold member 46, such that the first inner surface 40 and the second inner surface 48 face toward each other. These inner surfaces make up an inner cavity that is the desired shape of the compressed pledget 132. In the embodiment shown, both the first split cavity mold member 38 and the second split cavity mold member 46 have pores 22 located axially and radially along the mold.

The mold can be constructed from permeable materials or can be fabricated from impermeable or permeable materials, and then modified either mechanically, chemically, electrically, or a combination of the above to become permeable. Materials for the mold may include metals, polymers, composites, any other suitable material, or combinations of the above. Embodiments of the mold that are comprised of metals may include steel, stainless steel, copper, brass, titanium, alloys, aluminum, anodized aluminum, titanium, and combinations thereof. Embodiments of the mold that are comprised of polymers may include TEFLON®, polyethylene, polypropylene, polyester, polyolefins, polycarbonates, nylons, polyvinyl chloride, and mixtures thereof. One embodiment of a mold may be made of DELRIN® made by DuPont Plastics. Embodiments of the mold that are comprised of composites may include carbon fibers and blends of metal, epoxy, ceramic, and polymer blends. Other examples of suitable materials for the mold are foamed metals or plastics. The mold may be made of aluminum and epoxy porous aggregate, such as METAPOR BF100A1, available from Portec Ltd, Switzerland. Pores, interstices, or pathways can be produced in the above materials by any suitable operation, including, but not limited to, operations such as drilling, milling, punching, casting, injection molding, acid etching, electrical discharge machining, or any other suitable method.

In various embodiments used with the process of the present invention, the pledget may be maintained within a mold that comprises at least one pore along the length of the mold. The mold may have a plurality of pores in some embodiments. The pores can be on any location on the mold. In embodiments in which the mold is cylindrical, the pores may be located radially, axially, or both radially and axially. These pores may be macroscopic, microscopic, or submicroscopic. The pores may be of any suitable dimension. In some embodiments, the pores may range in diameter from about 0.2 mm to about 1.5 mm.

The process of the present invention may be used for stabilizing any type of tampon, including but not limited to the tampon disclosed in U.S. Pat. No. 6,258,075 and the shaped tampons disclosed in U.S. Pat. Nos. 6,824,536 and 6,932,805. Further, the process of the present invention may be used for the tampons having secondary absorbent members, disclosed in U.S. Publication No. 2005/0055003A1.

The absorbent material that comprises the pledget may be constructed from a wide variety of liquid-absorbing materials suitable for absorbent articles. Such materials include but are not limited to rayon (such as GALAXY Rayon and SARILLE L rayon, both available from Kelheim Fibres, GmbH., of Kelheim, Germany), cotton, folded tissues, woven materials, nonwoven webs, synthetic and/or natural fibers or sheeting, comminuted wood pulp which is generally referred to as airfelt, other suitable materials, or combinations of these materials. Other materials that may be incorporated into the pledget including peat moss, absorbent foams (such as those disclosed in U.S. Pat. Nos. 3,994,298 and 5,795,921), capillary channel fibers (such as those disclosed in U.S. Pat. No. 5,356,405), high capacity fibers (such as those disclosed in U.S. Pat. No. 4,044,766), superabsorbent polymers or absorbent gelling materials (such as those disclosed in U.S. Pat. No. 5,830,543), other suitable materials, and combinations of these. A more detailed description of liquid-absorbing materials shapes and dimensions can be found in U.S. Pat. No. 6,740,070.

The compressed product 20 stabilized by the process of the present invention may optionally include an overwrap comprising material such as, rayon, cotton, bicomponent fibers, polyethylene, polypropylene, other suitable natural or synthetic fibers known in the art, and mixtures thereof. In some embodiments, the tampon may include a nonwoven overwrap comprised of bicomponent fibers that have a polypropylene core surrounded by polyethylene manufactured by Vliesstoffwerke Christian Heinrich Sandler GmbH & Co.KG (Schwarzenbach/Saale, Germany) under the tradename SAS B31812000. In other embodiments, the tampon may comprise a nonwoven overwrap of a hydroentangled blend of about 50% rayon and about 50% polyester available as BBA 140027 produced by BBA Corporation of South Carolina, U.S. The overwraps may be treated to be hydrophilic, hydrophobic, wicking or non-wicking.

The compressed product stabilized by the process of the present invention may optionally include a withdrawal cord, a secondary absorbent member, an overwrap, a skirt portion, and/or an applicator. Withdrawal cords useful in the present invention may be made of any suitable material known in the prior art and include cotton and rayon. U.S. Pat. No. 6,258, 075 describes a variety of secondary absorbent members for use in pledgets. An example of a skirt portion is disclosed in U.S. Pat. No. 6,840,927.

Pressures and temperatures suitable for compression may be used. Typically, the absorbent material and the overwrap are compressed in the radial direction and optionally axially by any suitable means.

The compressed product stabilized by the present invention may be inserted digitally, or insertion may be aided through the use of any suitable applicator. When tampons or other products are to be digitally inserted, it may be desirable to provide a finger indent made using a compression rod at the withdrawal end of the tampon to aid in insertion. An example of a finger indent is found in U.S. Pat. No. 6,283,952. Applicators that may be used are "tube and plunger" or "compact" type arrangements and may be plastic, paper, or other suitable material.

Figure 4:
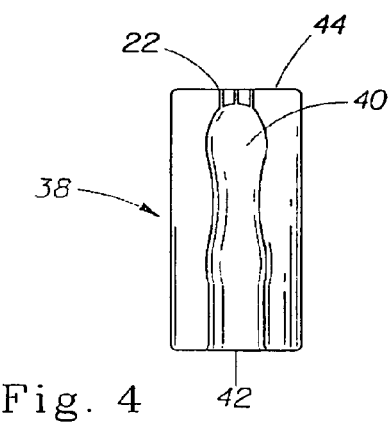
FIG. 4 is a plan view of a first split cavity mold member with pores located axially along the mold.
Figure 5:
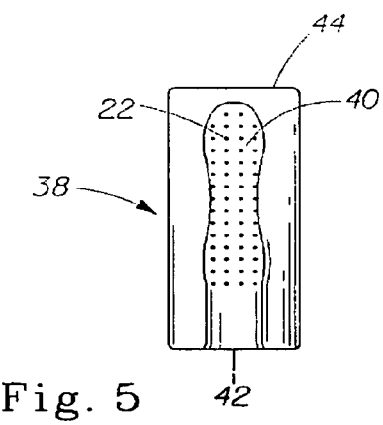
FIG. 5 is a plan view of a first split cavity mold member with pores located radially along the mold.

FIG. 4 and FIG. 5 show plan views of a first split cavity mold member 38 having a first inner surface 40. The first split cavity mold member 38 has a first end 42 and a second end 44. In the embodiment shown in FIG. 4, the first split cavity mold member 38 has pores 22 located axially along the first split cavity mold member 38. In the embodiment shown in FIG. 5, the first split cavity mold member 38 has pores 22 located radially along the first split cavity mold member 38.

Figure 6:
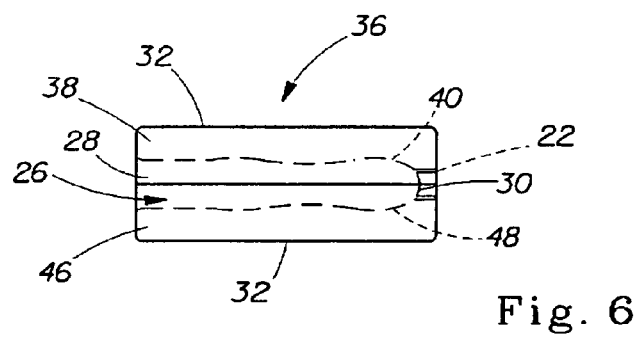
FIG. 6 is a side view of a split cavity mold with pores located axially along the mold.
Figure 7:
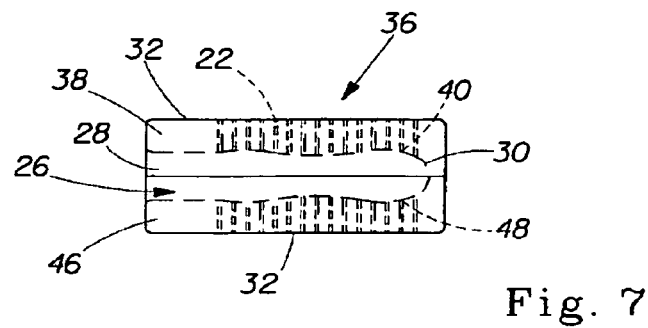
FIG. 7 is a side view of a split cavity mold with pores located radially along the mold.

FIG. 6 and FIG. 7 show a side view of the split cavity mold 36. The first split cavity mold member 38 and second split cavity mold member 46 are combined to form a split cavity mold 36. The first split cavity mold member 38 has a first inner surface 40 and an outer mold surface 32. The second split cavity mold member 46 is substantially similar, if not a mirror image or not identical in size, shape, and dimension, to the first split cavity mold member 38, and has a second inner surface 48 and an outer mold surface 32. The first split cavity mold member 38 and the second split cavity mold member 46 are configured such that the first inner surface 40 and the second inner surface 48 face each other and define an inner cavity 26 for shaping a pledget during compression, and/or retaining the shape for a compressed pledget subsequent to compression during the stabilization process. The inner cavity 26 has an open proximal end 28 and a closed distal end 30. In some embodiments, such as embodiments that combine compression and stabilization, the open proximal end 28 may act as an ingress port wherein the pledget is introduced in the inner cavity. In the embodiment shown in FIG. 6, the split cavity mold 36 has pores 22 located axially along the split cavity mold 36. In the embodiment shown in FIG. 7, the split cavity mold 36 has pores 22 located radially along the split cavity mold 36.

Figure 8:
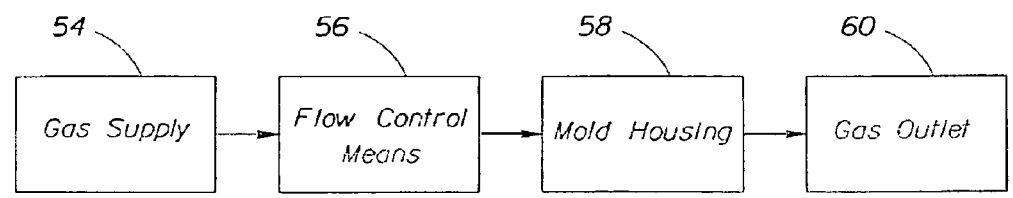
FIG. 8 is a diagram of one embodiment of a gas supply system in the process of the present invention.
Figure 9:
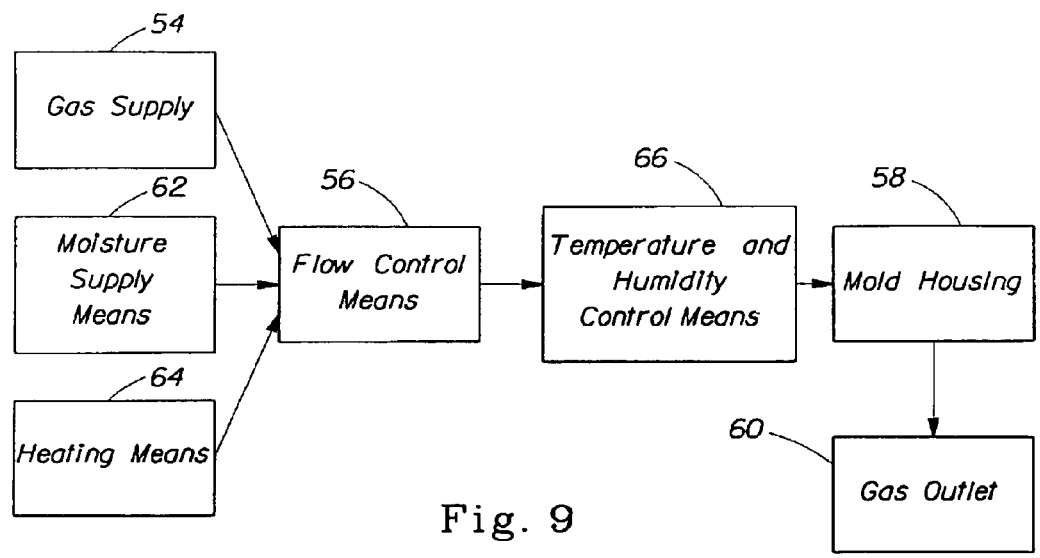
FIG. 9 is a diagram of another embodiment of a gas supply system of the process of the present invention.

FIG. 8 and FIG. 9 show a flow diagram of a process for using steam to stabilize the compressed pledget that may be used with the present invention. The process may comprise the steps of providing a compressed pledget and forcing gas through the compressed pledget. The compressed pledget may be maintained within a permeable mold during this process. In some embodiments of the process, the stabilized product may be produced in the presence of moisture. The moisture that is used in the process may be from the fibers of the material that comprises the pledget, within the gas that is introduced in the process, or both. In another embodiment of the process, the stabilization process may be combined with a compression process.

Any suitable targeted moisture content of the pledget after the stabilization process may be used. For example, the targeted moisture content may be from about 4% to about 15% of water by weight or any number within this range, or from about 8% to about 10% water by weight or any number within this range, as measured by the TAPPI method T 412.

The diagram in FIG. 8 shows that, in some embodiments, the process can be accomplished by providing a gas supply 54 opposed to a gas outlet 60, and a mold housing 58 oriented therebetween that contains the compressed pledget within the permeable mold. The incoming gas enters the machine at the gas supply 54. The rate of the gas flow can be varied by a flow control means 56.

The gases forced into the compressed pledget may be air, oxygen, nitrogen, argon, carbon dioxide, steam, ether, freon, inert gases, other suitable gases, and mixtures thereof. The supply of the gas may be varied by a flow control means 56. During the process of the present invention the gas may be propelled through the mold at any suitable rate, including at a rate of from about 0.2 to about 5.0 l/s. In some embodiments, the gas may be propelled for a time period ranging from about 1 s to about 20 s. In other embodiments, the gas may be propelled for a time period ranging from about 1 s to about 10 s. In other embodiments, the gas may be propelled from about 2 s to about 8 s.

The process of the present invention may comprise the step of heating the gas that is introduced to the compressed pledget. The process of the present invention may comprise the step of humidifying the gas that is introduced to the compressed pledget. As shown in FIG. 9, a moisture supply means 62, heating means 64, and a temperature and humidity control means 66 is added to the diagram of FIG. 8. As such, the heated and humidified gas flows into the mold housing 58 oriented therebetween that contains the compressed pledget within the permeable mold and flows out the gas outlet 60.

In embodiments of the process where the gas is heated, a heating means 64 may be used. The temperature may be varied by the temperature and humidity control means 66. In some embodiments, the gas is heated to a range of about 60° C. to about 210° C. In some embodiments, the gas may be heated to about 100° C., and in other embodiments the gas may be heated to about 163° C. The molds may be heated prior to insertion of the pledget within the mold. The molds may be heated prior to insertion of the pledget by hot air or alternate means, such as by conductive heating prior to insertion of the pledget. The mold can be heated to a temperature between about 38° C. and about 210° C., or any suitable temperature within this range. In some embodiments, the molds may be heated to about 71° C. In some embodiments, the process also may comprise the step of cooling the product. In some embodiments, the product may be cooled by air to ambient room temperatures from about 21° C. to about 24° C., or any suitable temperature within this range, or less than about 30° C.

In embodiments of the process where the gas is humidified, the moisture may be added via a moisture supply means 62. The humidity can be varied by a temperature and humidity control means 66. The moisture or humidity in the gas may be introduced by any suitable method, including but not limited to atomization, evaporation, steam blending, super heated steam blending, supersaturated steam blending, other suitable methods, or the like. The gas may be humidified to a range from about 1% to about 100% relative humidity, or any suitable number within this range, at the gas temperature.

FIG. 10 is a cross-sectional view of one embodiment 100 of the process of the present invention, including a pair of split molds: a compression mold 102 and a stabilization mold 104. In certain embodiments, the steps of compressing and stabilizing of the pledgets may be separated in order to reduce the complexity of the apparatus producing stabilized products, including products having a substantially serpentine shape and/or stabilized by the use of a gas.

In FIG. 10, both the compression mold 102 and the stabilization mold 104 are shown in their open positions 128 and aligned with a pledget infeed carrier 106 and a product discharge carrier 108. The embodiment 100 of FIG. 10 also shows a transfer member 110, or "pushrod," and a pledget 112 disposed in the pledget infeed carrier 106. The transfer member 110 can serve one or more functions, such as, for example: (a) transferring the pledget 112 through the sequence of process steps taking place during traveling of the pledget 112 from the pledget infeed carrier 106 to the compression mold 102, to the stabilization mold 104, and to the product discharge carrier 108; (b) compressing the pledget 112 longitudinally (in addition to the compression in the radial direction provided by the compression die 102, as described below); (c) forming a desired shape cavity at the base region of the product, suitable for the user's finger to facilitate digital insertion of the product into the vaginal (or other) cavity; and/or (d) providing a suitable seal for containing the gas inside the stabilizing die 104 during the stabilization treatment of the tampon.

The transfer member 110 may include at least one needle 138 extending from the transfer member 110 longitudinally for discharging a stabilized product from the split stabilization mold 104. The transfer member 110 may be aligned with the pledget infeed carrier 106, the compression mold 102, the stabilization mold 104, and the tampon discharge carrier 108 along a first longitudinal centerline L1.

It should be noted that the pledget having a secondary absorbent member extending from the base region of the pledget may be loaded into the pledget infeed carrier with the secondary absorbent member being diverted radially in relation to the pledget to ensure that the secondary absorbent member does not interfere with the movement of the transfer member 110. This may reduce or prevent pushing the secondary absorbent member into the base region of the pledget. The radial diversion of the secondary absorbent member (including with at least one cord extending also from the base region of the tampon) can be provided during loading of the pledget 112 by any suitable means, for example, a plate disposed in the direction of loading of the pledget into the cavity of the infeed carrier. Alternatively, a vacuum tube could be used.

FIG. 11 is a cross-sectional view of the pledget infeed carrier 106 of FIG. 10, taken along line 11-11. The pledget infeed carrier 106 includes a cavity 120 that can be suitably shaped to accept the pledget 112, which is shown as being folded to form an M-shape configuration. However, alternatively, the pledget 112 can be not folded or folded into any suitable configuration. The pledget infeed carrier 106 can be made from any material suitable for producing products according to the present invention.

FIG. 12 is a cross-sectional view of the split compression mold 102 of FIG. 10, taken along line 12-12. The split compression mold 102 includes a first member 122 and a second member 124. At least one of the members 122 and 124 is capable of moving in a direction R to effect an open position 128 or a closed position 129 (shown as an interrupted line) of the split compression mold 102. In the closed position 129, the inner surface 127 of the compression mold 102 forms a cross-section of any desired shape, such as a generally circular cross-section of a desired diameter, for example, a diameter D of about 12.5 mm. The inner surface 127 can be of any suitable shape and of any desired dimension. The split compression mold 102 can be made from any materials capable of providing desired compression forces and suitable for producing products according to the present invention.

FIG. 13 is a cross-sectional view of the split stabilization mold 104 of FIG. 10, taken along line 13-13. The split stabilization mold 104 can be similar in the dimensions and makeup, in all or any aspects, to the split mold 36 shown in FIGS. 3-7 and described in more detail above. For example, similarly to the split mold 36 of FIGS. 3-7, the split stabilization mold 104 includes the first member 38, the second member 46, and at least one pore 22 suitable for providing a gas flow inside the inner surface of the stabilization mold 104. The split stabilization mold 104 is shown in the open position 128 when the first member 38 and the second member 46 are separated from each other. At least one of the mold members 38 and 46 can move in the direction R to effect the open position 128 or the closed position 129 (shown as an interrupted line) when the first member 38 and the second member 46 are in contact with each other.

FIG. 14 is a cross-sectional view of a product discharge carrier 108 of FIG. 10, taken along line 14-14. The product discharge carrier 108 includes a cavity 130 that can be suitably dimensioned and shaped to accept the stabilized product.

In one embodiment of the present invention, the cavity 130 may be defined by a multiplicity of longitudinal flutes 133 to facilitate the dissipation of a gas forced into the cavity 130 during the stabilization process of the present invention. The product discharge carrier 108 can be made from any material suitable for producing products in accordance with the present invention.

Figure 15:
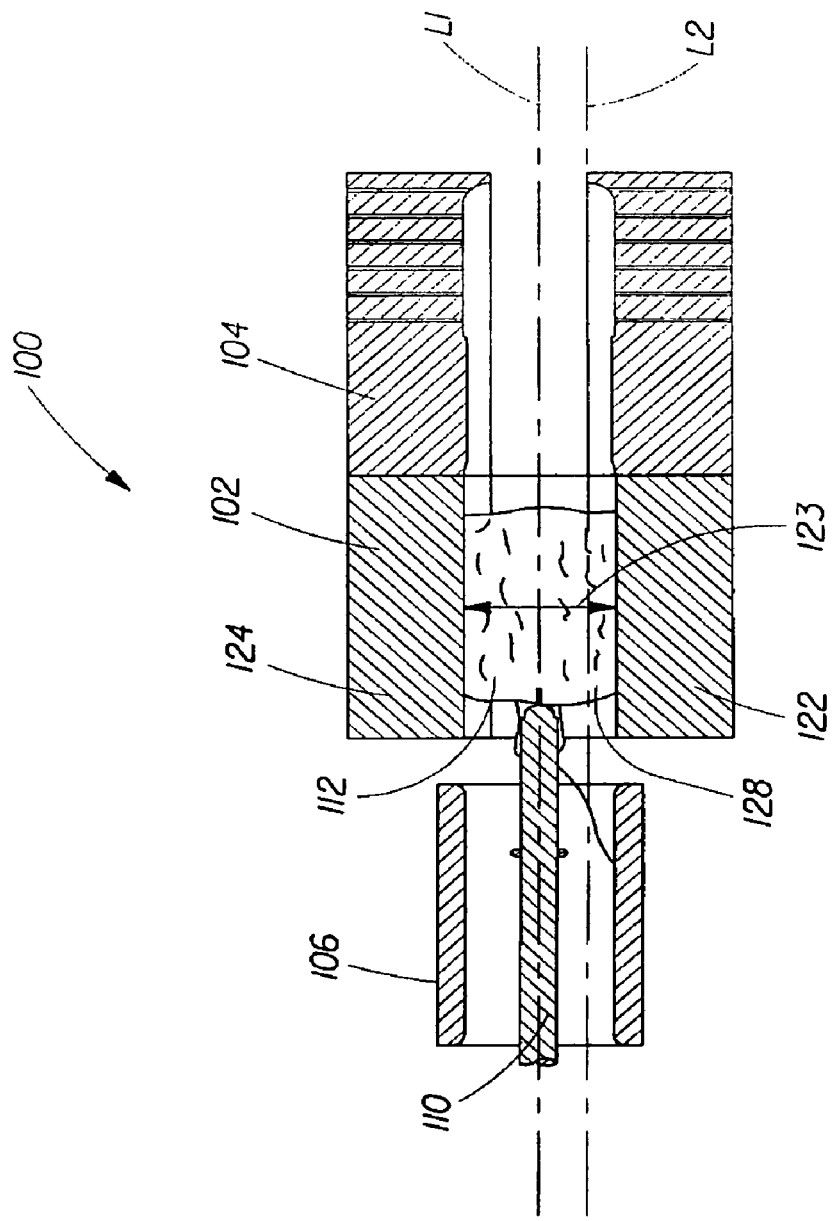
FIG. 15 is a cross-sectional view of an embodiment of the present invention showing a pledget being loaded into the split compression mold by a transfer member, the split compression mold being in an open position.

FIG. 15 is a cross-sectional view of an embodiment of the present invention showing pledget 112 being loaded into the split compression mold 102 by the transfer member 110 when the split compression mold 102 is in the open position 128 and the transfer member 110 is aligned with the first longitudinal centerline L1. In the open position 128, the compression mold 102 has an inside dimension 123 that can be any dimension suitable for accepting the pledget 112. For example, in one embodiment of the invention, the inside dimension 123 may be from about 25 mm to about 80 mm, or any number in this range. In certain embodiments, the inside dimension 123 is about 40.5 mm.

Figure 16:
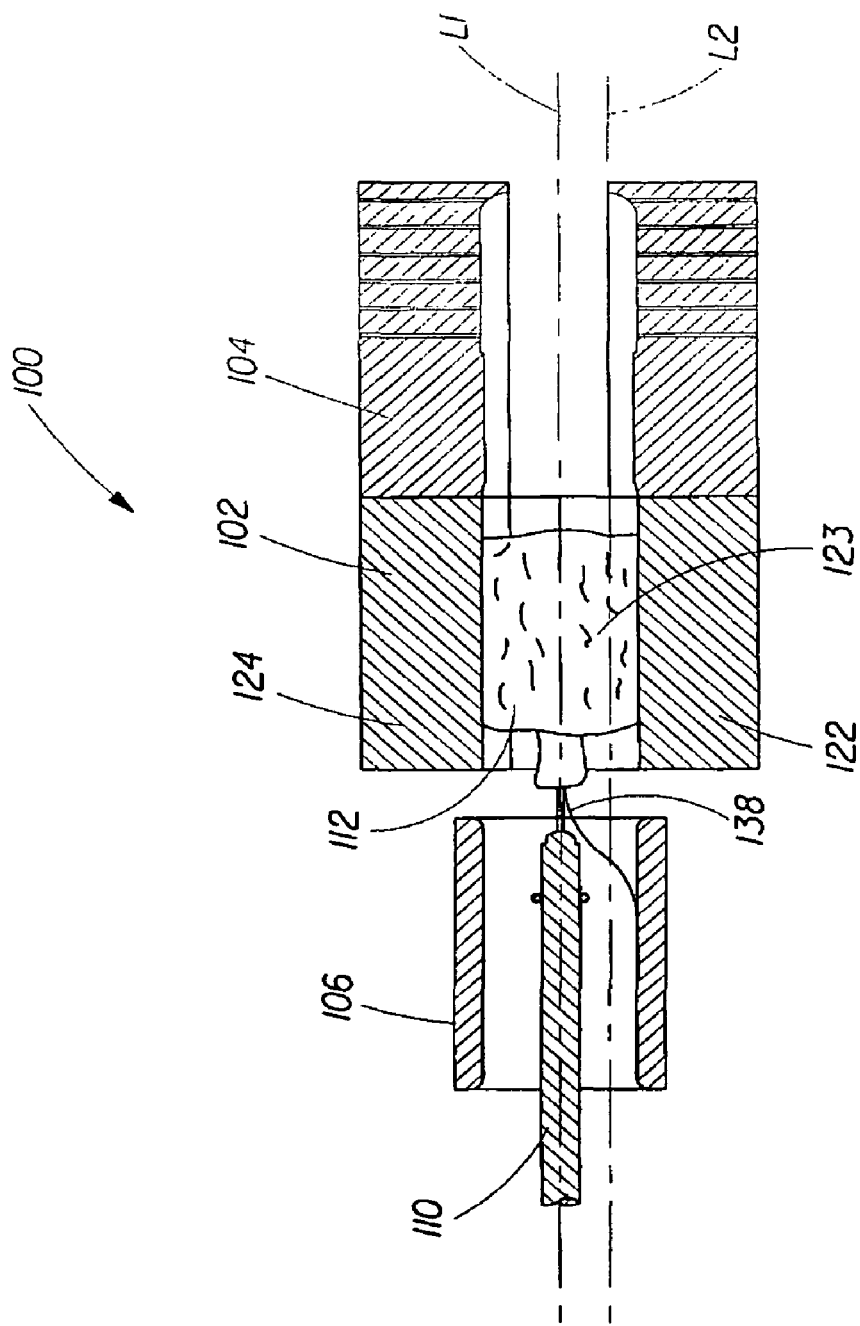
FIG. 16 is a cross-sectional view of an embodiment of the present invention showing a transfer member being detracted from the pledget.

FIG. 16 is a cross-sectional view of an embodiment of the present invention showing a transfer member 110 being retracted from the pledget 112 with the pledget 112 loaded in the compression mold 102. It should be noted that the transfer member may be detracted from the pledget 112 to detract the needle(s) 138 from the pledget 112 prior to the compression of the pledget 112. However, other contemplated embodiments of the transfer member 110 may allow the needle(s) 138 to move inside the transfer member 110 to protrude from or hide inside the transfer member 110, thus eliminating the need for the retraction of the transfer member 110.

It should be also noted that other contemplated embodiments of the split compression and stabilization molds 102 and 104, respectively, may include both moving mold members, in contrast to embodiments including a moving mold member and a fixed mold member. When both moving mold members are employed, the transfer member 110 does not need to move in the direction R for closing and opening of the molds.

Figure 17:
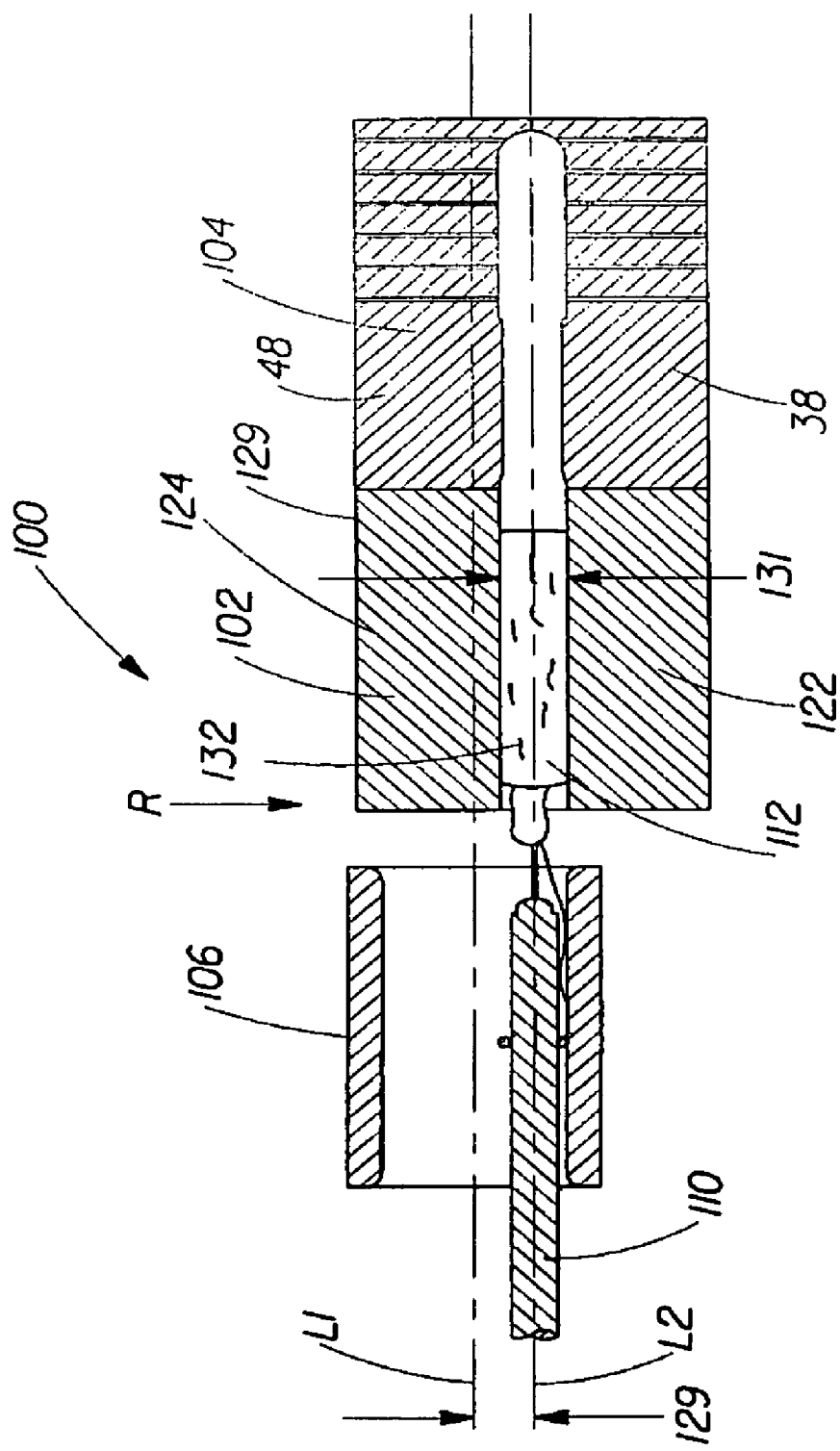
FIG. 17 is a cross-sectional view of an embodiment of the present invention showing a pledget being compressed into a compressed pledget in the compression mold.

FIG. 17 is a simplified cross-sectional view of an embodiment of the present invention showing pledget 112 being compressed into a compressed pledget 132 in the compression mold 102 when the compression mold 102 is in the closed position 129. In the closed position 129, the compression mold 102 has an inside dimension 131 that can be any dimension suitable for compressing the pledget 112 into a desired compressed dimension. For example, in one embodiment of the invention, the inside dimension 131 is compressed to about 12.5 mm. The pledget 112 may be partially compressed in compression mold 102, thereby forming the compressed pledget 132, and the compressed pledget 132 is then further compressed or compacted when the transfer member 110 loads the compressed pledget 132 into the stabilization mold 104.

The closed position 129 may be accomplished by moving the first compression mold member 122 in the direction R toward the second compression mold member 124. However, as noted above, other contemplated embodiments of the present invention can include both moving mold members. During the closing of the compression mold 102, the pledget 112 undergoes a radial compression in the direction R, reducing the radial dimension of the pledget to the inside dimension 131, which may be any suitable dimension, for example, about 12.5 mm. Thus, in one example, the first compression mold member 122 moved radially from about 40.5 mm to about 12.5 mm, resulting in a total movement of about 28 mm.

As shown in FIG. 17, the transfer member 110 also moved in the direction R to become aligned along a second longitudinal centerline L2 aligned with the closed position 129 of the compression mold 102. The distance between the first longitudinal centerline L1 and the second longitudinal centerline L2 is a dimension 129, which may be about half of the radial movement of the first compression mold member 122. For example, in the particular example above, when the first compression mold member 122 moves about 28 mm, the transfer member 112 moves the distance 129 of about 14 mm.

Figure 18:
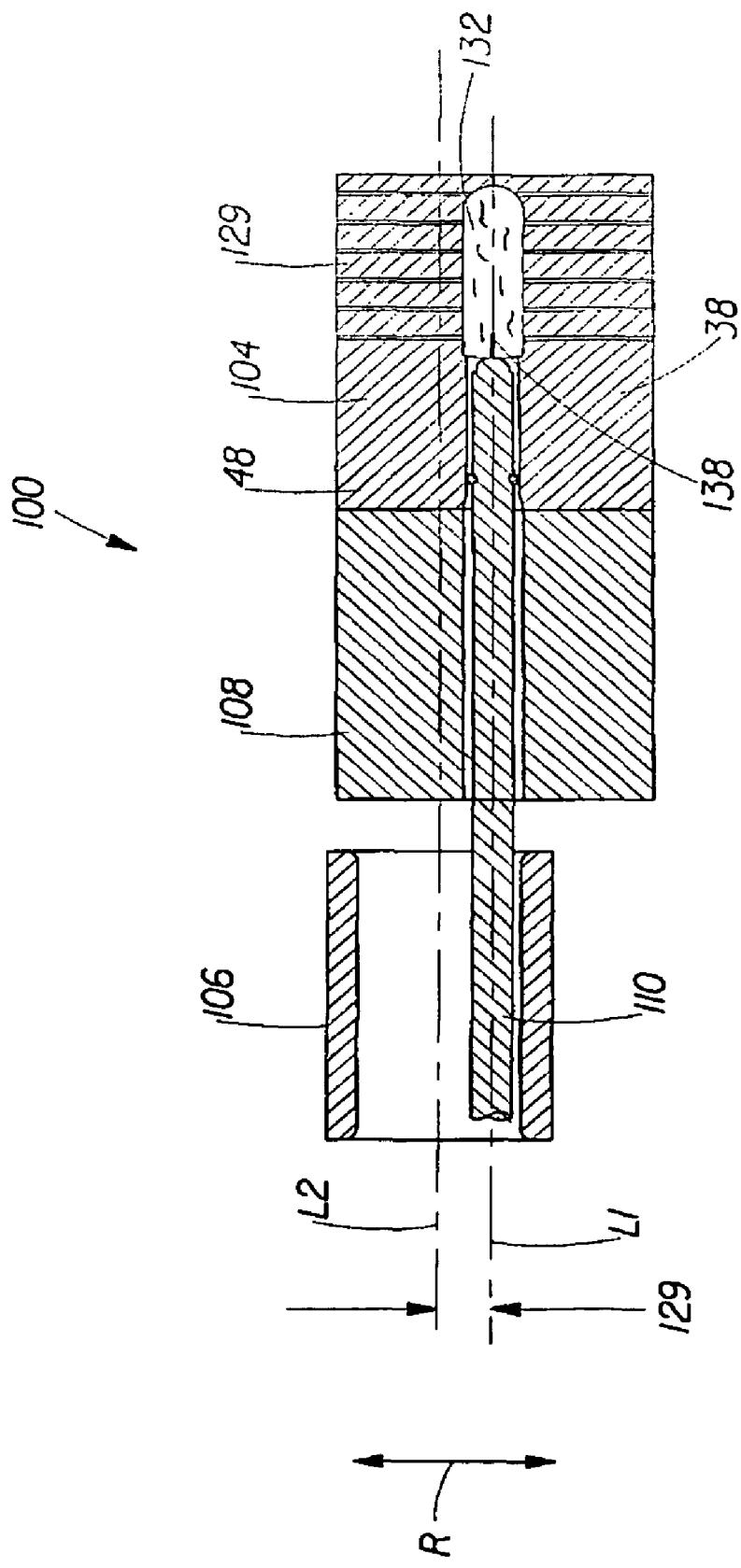
FIG. 18 is a cross-sectional view of an embodiment of the present invention showing a compressed pledget being loaded into the stabilization mold.

FIG. 18 is a simplified cross-sectional view of an embodiment of the present invention showing compressed pledget 132 being loaded into the split stabilization mold 104 by the transfer member 110 when the split stabilization mold 104 may be in the closed position 129 and aligned with the second longitudinal centerline L2. In one embodiment, the closed position 129 of the stabilization mold 104 is accomplished by moving the first member 38 of the stabilization mold 104 in the direction R simultaneously with the first compression mold member 122, as shown in FIG. 17. However, as was noted above with respect to the compression mold 102, the stabilization mold 104 can also include two moving mold members. Furthermore, in other contemplated embodiments of the present invention, the compression mold 102 and the stabilization mold 104 do not need to close and open simultaneously.

Figure 19:
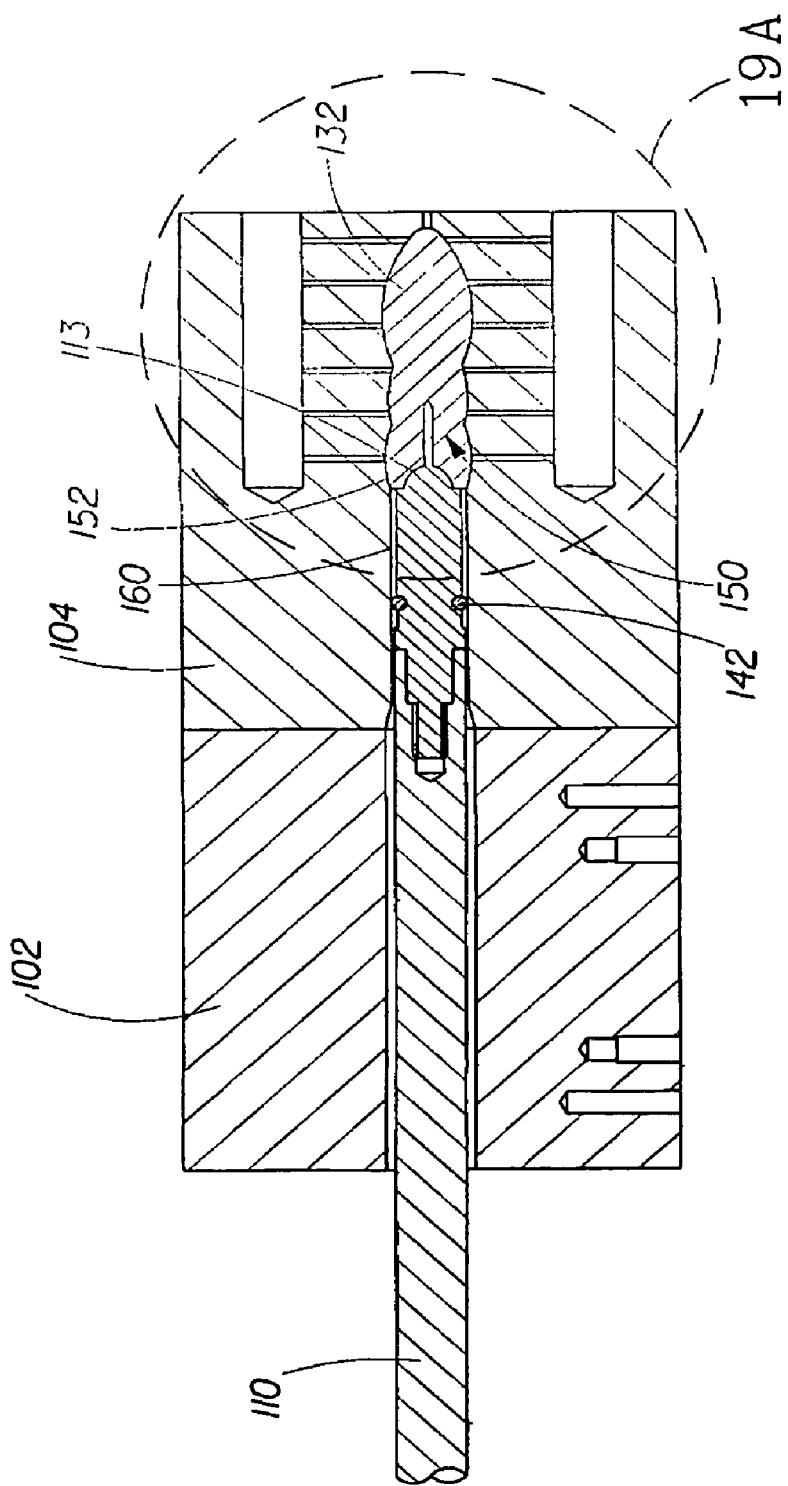
FIG. 19 is a cross-sectional view of one embodiment of the transfer member loading a compressed pledget into a stabilization mold when the transfer member has completed the loading stroke.
Figure 19A:
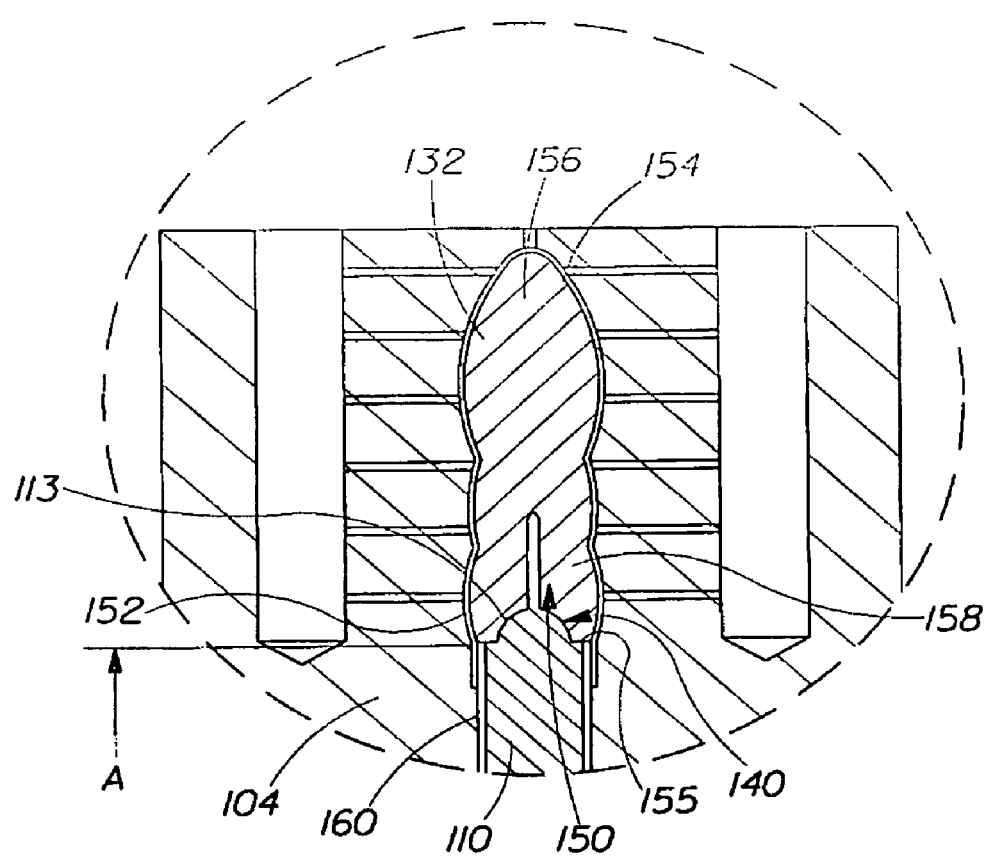
FIG. 19A is a more detailed view of the stabilization mold shown in FIG. 19.
Figure 20:
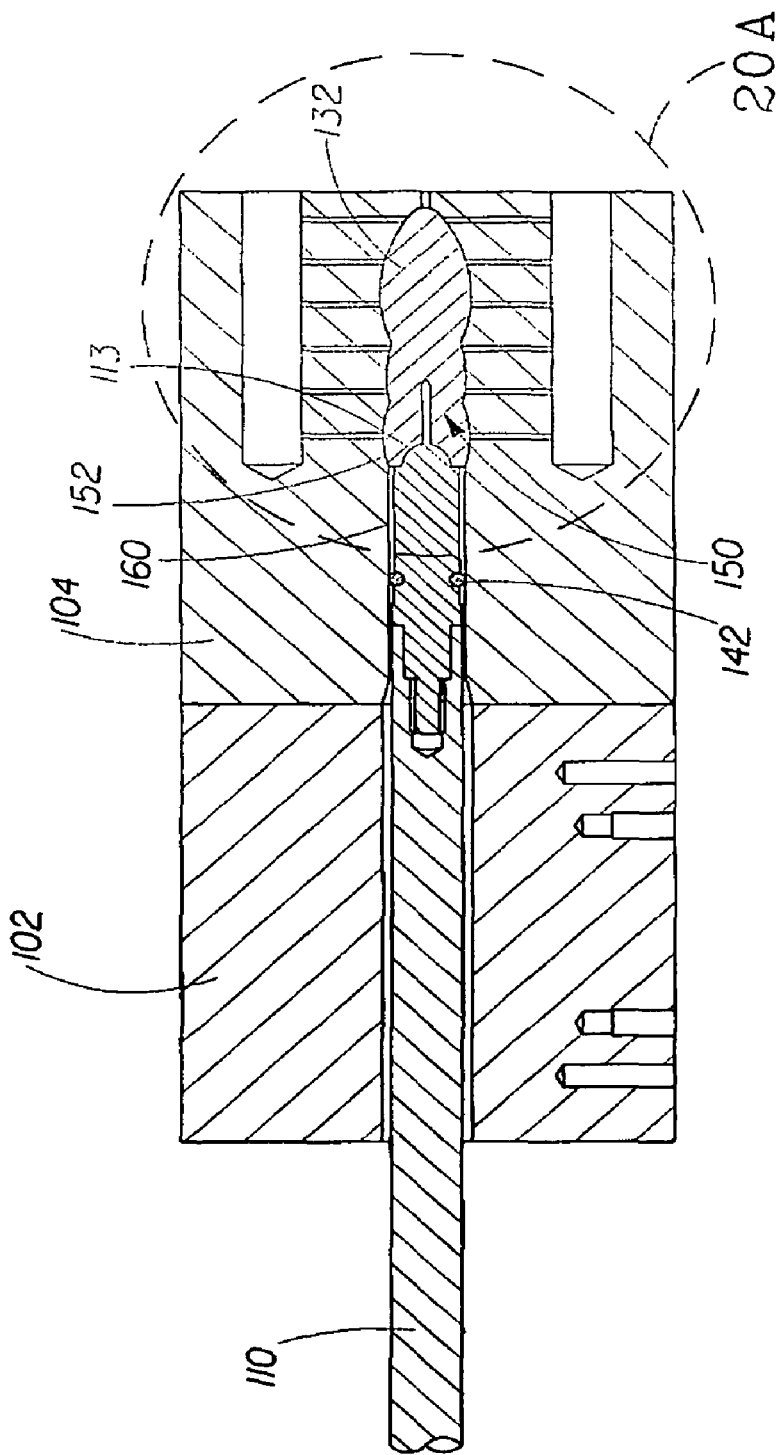
FIG. 20 is a cross-sectional view of one embodiment of the transfer member 110 in a stopped position subsequent to the controlled retraction of the transfer member 110.
Figure 20A:
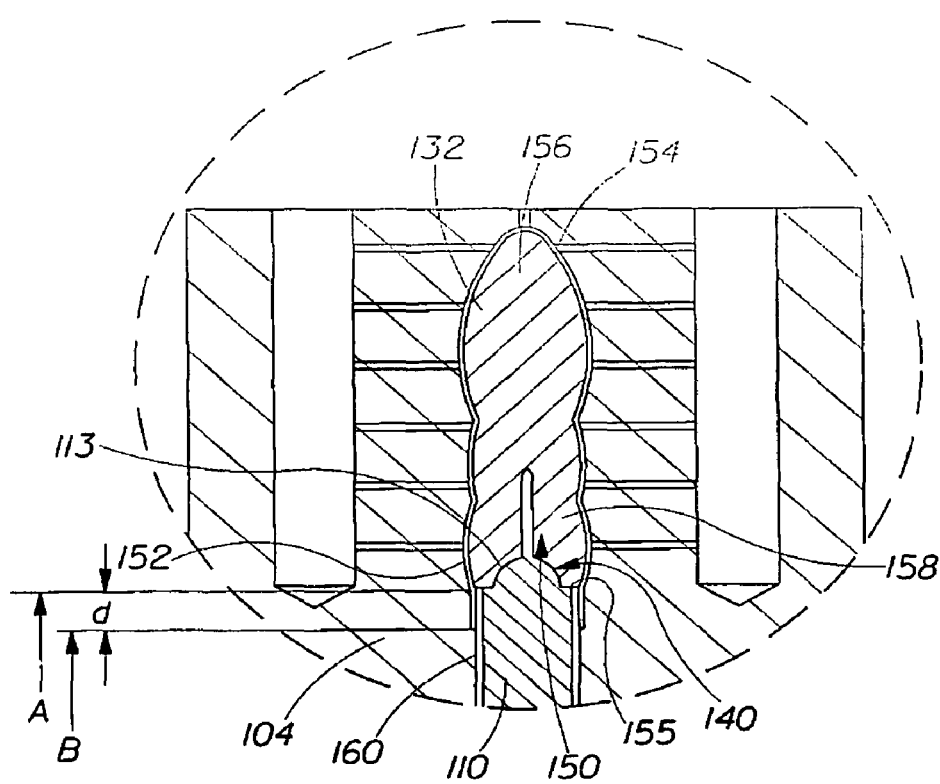
FIG. 20A is a more detailed view of the stabilization mold shown in FIG. 20.

The transfer member 110 may load the compressed pledget 132 into the stabilization mold 104 with a controlled loading stroke that is followed by a controlled transfer member retraction prior to stabilizing the compressed pledget 132 in the stabilization mold 104. FIG. 19 is a cross-sectional view of one embodiment of the transfer member 110 loading the compressed pledget 132 into the stabilization mold 104 when the transfer member has completed the loading stroke. FIG. 19A is a more detailed view of the stabilization mold 104 shown in FIG. 19. FIG. 20 is a detailed cross-sectional view of one embodiment of the transfer member 110 in a stopped position subsequent to the controlled retraction of the transfer member 110, and FIG. 20A is a more detailed view of the stabilization mold 104 shown in FIG. 20.

With reference to FIG. 19, the controlled loading stroke of the transfer member 110 may load the compressed pledget 132 through an inlet region 160 of the stabilization mold 104 and then into an inner cavity 150 of the stabilization mold 104 through an open proximal end 152 of the inner cavity 150. With reference to FIG. 19A, during the loading stroke the transfer member 110 forces the compressed pledget 132 through proximal end 152 of inner cavity 150 and continues advancing the compressed tampon 132 so that the compressed pledget fills the stabilization mold and conforms to the shape of the inner cavity 150. In FIG. 19A and in FIG. 20A, the mold is shown in double lines to illustrate the relative positioning of the pushrod and the pledget in the mold. Upon completion of the loading stoke, a head region 156 of the compressed pledget 132 may fill a closed distal end 154 of the inner cavity 150. In one embodiment, the region of the compressed pledget 132 that is loaded into the distal end 154 of the inner cavity 150 may be the insertion end of the product. In another embodiment, the region of the compressed pledget 132 that is loaded into the distal end 154 of the inner cavity 150 may be the withdrawal end of the product.

During the loading stroke the transfer member 110 advances to an adjustable and predetermined loading position. In the embodiment shown in FIG. 19A, the loading position is identified where tip 113 of the transfer member 110 is aligned with loading position A.

In one embodiment, the loading position may be established by determining when a desired density is achieved in the compressed pledget. Upon completion of the loading stoke but prior to the controlled retraction, the fiber density throughout the compressed pledget 132 may be non-uniform such that the fiber density of the compressed pledget at the base region 158 of the compressed pledget is greater than the fiber density of the compressed pledget material at the head region 156 of the compressed pledget. In certain embodiments, where the compressed pledget is constructed from synthetic and natural fibers or other liquid-absorbing material as previously described, the loading position may be determined by ascertaining the endpoint of a loading stroke that creates a fiber density in the compressed pledget at the head region 156 that is at least 0.3 g/cc. In other embodiments, the loading position may be determined by ascertaining the endpoint of a loading stroke that creates a fiber density in the compressed pledget material at the head region 156 that is at least about 0.36 g/cc or higher.

The loading position may be determined by ascertaining a corresponding density in the compressed pledget at the head region 156 that achieves desired stability and aesthetics, such as smoothness and surface finish, for the product that is formed from the compressed pledget. In certain embodiments, the desired aesthetics or smoothness for a product formed from the compressed pledget may include a surface finish having one or more of the following physical characteristics: no unintended cracks having a width greater than about 1 mm, no unintended cracks that extend into a middle region of the tampon having a width greater than about 0.5 mm, no unintended divots having an area greater than about 4 $mm^2$, and no unintended divots in the head region.

With reference to FIG. 20, the controlled loading stroke may be followed by a controlled retraction, whereby transfer member 110 retracts a predetermined distance in a direction substantially opposite the loading stroke prior to stabilizing the compressed pledget 132 in the stabilization mold 104. The controlled retraction may be substantially immediately after the controlled loading stroke, or it may be done at any suitable time thereafter. The transfer member 110 typically retracts such that transfer member 110 remains in contact with pledget 132 during the retraction and the compressed pledget 132 is maintained in the stabilization mold at its base region by the transfer member 110. During the retraction, the material in the base region 158 of the compressed pledget 132 may rebound in a radial direction, in an axial direction, or both. With reference to FIG. 20A, during the controlled retraction the transfer member 110 retracts to a predetermined final molding position, thereby releasing a certain level of the stress in the compressed fiber, or other material used to construct the compressed pledget, typically at least in the base region 158 of the compressed pledget 132.

As shown in FIG. 20A, the molding position is identified where tip 113 of the transfer member 110 is aligned with molding position B, and during the controlled retraction the transfer member travels distance d. In one embodiment, the retraction distance d is between about 3 mm and about 4 mm or any number within this range. A retraction distance d may be selected by ascertaining a distance that maintains a minimum desired density in the base region 158 of the compressed pledget 132. Such a distance may be determined as a function of one or more of a length of inner cavity 150 or other geometries and design aspects of inner cavity 150, the loading position A, an ability of the compressed pledget 132 to be subsequently stabilized, a resultant exterior smoothness of a stabilized product formed from the compressed pledget 132, and absorbent and aesthetic qualities of a stabilized product formed from the compressed pledget 132. A retraction distance d may be selected by determining a distance that causes tip 113 of the transfer member 110 to remain in contact with the compressed pledget 113.

The molding position B may also correspond to the final tampon molding position and length, and the length of the stabilization mold 104 may be configured to sequester the rebounding fiber of the base region 158 in concert with the tip 113 of the transfer member 110. The tip 113 maintains compression on the compressed pledget 132 when the transfer member 110 comes to rest subsequent to the controlled retraction and sustains its position during the stabilization process as described below. The tip 113 may also include a seal 142 capable of sealing the cavity 150 of the stabilization mold 104 to contain the gas and prevent unintentional or undesirable gas flow down the inlet region 160 of the stabilization mold 104 that will be injected into the inside of the stabilization mold 104 during the stabilization treatment of the compressed pledget.

The final molding position may be adjustable, and in one embodiment the final molding position may be identified by determining when a desired density is achieved in the material of the base region 158 of the compressed pledget. In the embodiment described above where the fiber density created in the compressed pledget material at its head region 156 is at least about 0.3 g/cc upon completion of the loading stoke, the final molding position may be determined whereby the fiber density created at the base region 158 of the compressed pledget is at least about 0.3 g/cc, 0.36 g/cc, or 0.46 g/cc.

The final molding position may also be determined whereby the fiber density created at the base region 158 of the compressed pledget has an upper limit that correlates to a stabilized tampon formed from the compressed pledget that has desired absorptive qualities or has a generally smooth exterior surface. In certain embodiments, the desired smoothness of the exterior surface of a product formed from the compressed pledget may include a product surface finish having one or more of the following physical characteristics: no unintended cracks having a width greater than about 1 mm, no unintended cracks that extend into a middle region of the tampon having a width greater than about 0.5 mm, no unintended divots having an area greater than about 4 mm$^2$, and no unintended divots in the head region. In another embodiment, the desired smoothness may include a product having one or more of the following physical characteristics at the exterior surface of the base region 158 of the tampon, including the exterior surface of cavity 140 in the base region: no unintended cracks having a width greater than about 1 mm and no unintended divots having an area greater than about 4 mm$^2$. The final molding position may be determined whereby the fiber density created at the base region 158 of the compressed pledget creates a desired stress gradient or density gradient from the base region 158 to the head region 156 of the compressed pledget 132.

During the controlled retraction, the release of stress in the material of the compressed pledget may be realized to a greater degree in the base region 158 than the head region 156, thereby allowing the stress of the base region material to be set by the controlled retraction without substantially affecting the stress of the head region material. By so establishing the loading position A and the final molding position B, the uniformity of the compressed pledget's density gradient prior to stabilization may be increased, the stress relaxation losses for the stabilized product will be reduced particularly in the base region thereby increasing the future maximum product expansion. In addition, the controlled retraction can be calibrated to reduce or eliminate flashing, yield a product formed from the compressed pledget with a generally smooth exterior, and to make the tampon's base region more regularly shaped.

Table 1 below presents dimension data for a compressed pledget 132 that is loaded into an inner cavity 150 having a length of about 50 mm, a cavity distal end diameter of about 14.6 mm at the distal end's widest point, a cavity middle region diameter of about 12.6 mm at the middle region's narrowest point, and a cavity proximal end diameter of about 15.6 mm at the proximal end's widest point, and where transfer member 110 is advanced to a loading position A that generates at least about 0.36 g/cc in head region 156 of the tampon. The values in Table 1 present the diameters of the resulting tampon, after removal from the mold, at its head region, middle region, and base region, and the tampon length, after the transfer member 110 advances to a loading position A that initially compresses the pledget longitudinally to about 46 mm, about 47 mm, and about 48 mm (rows 1, 2, and 3 respectively), as measured from the rim 155 of the tip 113, and then retracts to a molding position B where the rim 155 of the tip 113 of the transfer member 110 is about 51 mm from the opposing end of the inner cavity 150. More precisely, in each instance shown in Table 1, the rim 155 of the tip 113 of transfer member 110 retracts about 1 mm deep into the inlet region 160, as shown in FIG. 20A at position B, into which the compressed pledget material may rebound during retraction. In this example, the height of the dome-shaped tip 113 is about 7 mm, though any suitable height may be used. Using the methods of the present invention, the resulting tampon better corresponds dimensionally to the mold that is used to make it, including in the base region.

TABLE 1

| Pledget Length at Loading Position | Tampon Head Region | Tampon Middle Region | Tampon Base Region | Tampon Length |
| --- | --- | --- | --- | --- |
| 46 mm | 14.66 | 12.39 | 14.08 | 46.97 |
| 47 mm | 14.60 | 12.36 | 14.15 | 48.87 |
| 48 mm | 14.59 | 12.33 | 14.62 | 50.63 |

Retracting transfer member 110 from loading position A to molding position B prior to stabilizing the compressed pledget 132 may enhance performance of a tampon formed from the compressed pledget. Table 2 below presents tampon product expansion profiles for a tampon formed from a compressed pledget 132 that is loaded into an inner cavity 150 having a length of about 50 mm, a cavity distal end diameter of about 14.6 mm, a cavity middle region diameter of about 12.6 mm, and a cavity proximal end diameter of about 15.6 mm. Table 2 provides the radial, or "widthwise," expansion data of tampons as percentages of their pre-expansion radii. The values shown in Table 2 were derived using the Expansion Under Pressure Test Method, described below.

As can be seen in Table 2, retraction enhances the extent to which the radial expansion in the head region more closely correlates with the radial expansion in the base region. Using the method and apparatus of the present invention, the uniformity of the radial expansion along the length of the tampon may be enhanced. The method and apparatus may be used to achieve a suitable or desired level of expansion uniformity, such as the head region having a head region expansion that is at least about 60%, at least about 70%, at least about 80%, at least about 85%, at least about 90%, at least about 95%, or more of a base region expansion of said base region.

TABLE 2

|  | Head Region Radial Expansion | Middle Region Radial Expansion | Base Region Radial Expansion |
| --- | --- | --- | --- |
| shaped tampons without retraction | 27% | 53% | 41% |
| shaped tampons with retraction | 43% | 64% | 46% |
| cylindrical tampons (without transfer member control during stabilization) | 29% | 28% | 29% |

Without the use of transfer member control, the cylindrical tampons referred to above in Table 2 do not have a high surface finish as described herein, and their levels of expansion are lower than those for tampons made by the present methods, as shown above. Shaped tampons without the use of retraction may have lower levels of expansion. Using the methods disclosed herein, higher levels of expansion may be delivered. A greater ratio of tampon head expansion versus base expansion also may be delivered.

The above performance may be delivered by molds wherein the proximal end of the mold corresponds to the base of the tampon. In other embodiments, the loading direction may be reversed, such that the distal end may corresponds to the base of the tampon. In such cases, higher levels of head expansion may be delivered, which may exceed that of the tampon base. As can be seen in Table 2, the product may expand at least 20% in each of its head, middle, and base regions, or along its entire length; at least 30% in each of its head, middle, and base regions, or along its entire length; or at least 40% in each of its head, middle, and base regions, or along its entire length. Further, the ratio of the head region radial expansion to the base region radial expansion can be about 100%, between about 100% and about 105%, or greater. For example, when the loading direction is reversed, the head region radial expansion could be about 46% and the base region radial expansion could be about 43% (head region radial expansion and base region radial expansion percentages are reversed from those shown in Table 2 for shaped tampons).

Table 3 below presents tampon product expansion profiles for a compressed pledget 132 that is loaded into an inner cavity 150 having a length of about 50 mm, a cavity distal end diameter of about 14.6 mm, a cavity middle region diameter of about 12.6 mm, and a cavity proximal end diameter of about 15.6 mm. Table 3 demonstrates increased radial expansion distances of tampons formed with transfer member retraction relative to the radial expansion distances measured in tampons formed without retraction.

TABLE 3

|  | Head Region Expansion | Middle Region Expansion | Base Region Expansion |
| --- | --- | --- | --- |
| shaped tampons initial, without retraction | 14.6 mm | 12.4 mm | 14.8 mm |
| shaped tampons final, without retraction | 18.5 mm | 19.0 mm | 20.9 mm |
| shaped tampons initial, with retract | 14.8 mm | 12.9 mm | 15.4 mm |
| shaped tampons final, with retraction | 21.1 mm | 21.1 mm | 22.5 mm |
| cylindrical tampons initial, (without transfer member control during stabilization) | 15.3 mm | 15.3 mm | 15.3 mm |
| cylindrical tampons final, (without transfer memberl control during stabilization) | 19.8 mm | 19.6 mm | 19.7 mm |

The process of advancing a compressed pledget 132 into the stabilization mold 104 with a controlled loading stroke followed by a controlled retraction is suitable for loading the compressed pledget in a stabilization mold conforming to the shape and dimensions of stabilization mold 104, shown in FIGS. 19, 19A, 20, and 20A. The process is also appropriate for a variety of other mold shapes and patterns including cylindrical molds and other shapes. In one embodiment, the stabilization mold has a length of about 46 mm, measured from a lower ledge proximate the open proximal end 152 of the mold's inner cavity 150 to a tip proximate the closed distal end 154 of the mold's inner cavity. In another embodiment, the stabilization mold has a length of about 51 mm. Other mold shapes and patterns that have not been explicitly described herein are nonetheless within the scope of the invention. The loading position and molding position may be selected based on the mold's geometry to achieve a more regularly shaped tampon base region that more closely corresponds to the stabilization mold's form subsequent to the stabilization treatment and removal from the mold, as shown in Table 1.

Additionally, the loading stroke and controlled retraction of the transfer member 110 may be adjusted to accommodate both the specific mold and compressed pledget material, such that appropriate density and stress are delivered to both the head region and the base region of the compressed pledget. When the compressed pledget fiber, fiber blends, moisture level, or other material used for constructing the compressed pledget are altered, the pledget's stress sensitivity also may be altered. Further the compressed pledget may be advanced in the mold in various configurations, including a folded, serpentine, or rolled arrangement. An intended loading position and intended molding position may be redefined accordingly to achieve the desired uniform density in the compressed pledget based on the material and arrangement of the compressed pledget, whereby the density in the head region and the base region are substantially the same. Alternatively, the desired loading position and desired molding position may be redefined accordingly to achieve the desired density in the head region 156 and the desired density in the base region 158, where the density in the head and base regions is non-uniform, whereby the density in the head region 156 is greater than the density in the base region 158.

In addition to differing stabilization mold shapes and dimensions, the process of advancing a compressed pledget 132 into the stabilization mold 104 with a controlled loading stroke followed by a controlled retraction is also appropriate for a variety of transfer member shapes. Particularly, the tip 113 of transfer member 10 may have a variety of dome depths and radii and a variety of rim 155 dimensions. The tip 113 engages the base region 158 of the compressed pledget 132 during the controlled loading stroke and retraction, and may be selected to achieve a desired shape for the base region 158. A suitably shaped tip 113 may form a cavity 140 in base region 158 of the compressed pledget 132, suitable for the user's finger to facilitate digital insertion of the tampon into the vaginal cavity. The tip 113 may also include a seal 142 capable of sealing the cavity of the stabilization mold 104 to contain the gas that will be injected into the inside of the stabilization mold 104 during the stabilization treatment of the compressed pledget, as described below. Examples of apparatuses and methods for sealing the cavity of the stabilization mold are described in U.S. application Ser. No. 11/595,322 entitled "System and Method for an Expandable Pushrod Mold Seal" and filed in the names of Steven Ray Gilbert and Joseph Michael Manton, on Nov. 10, 2006.

Figure 21:
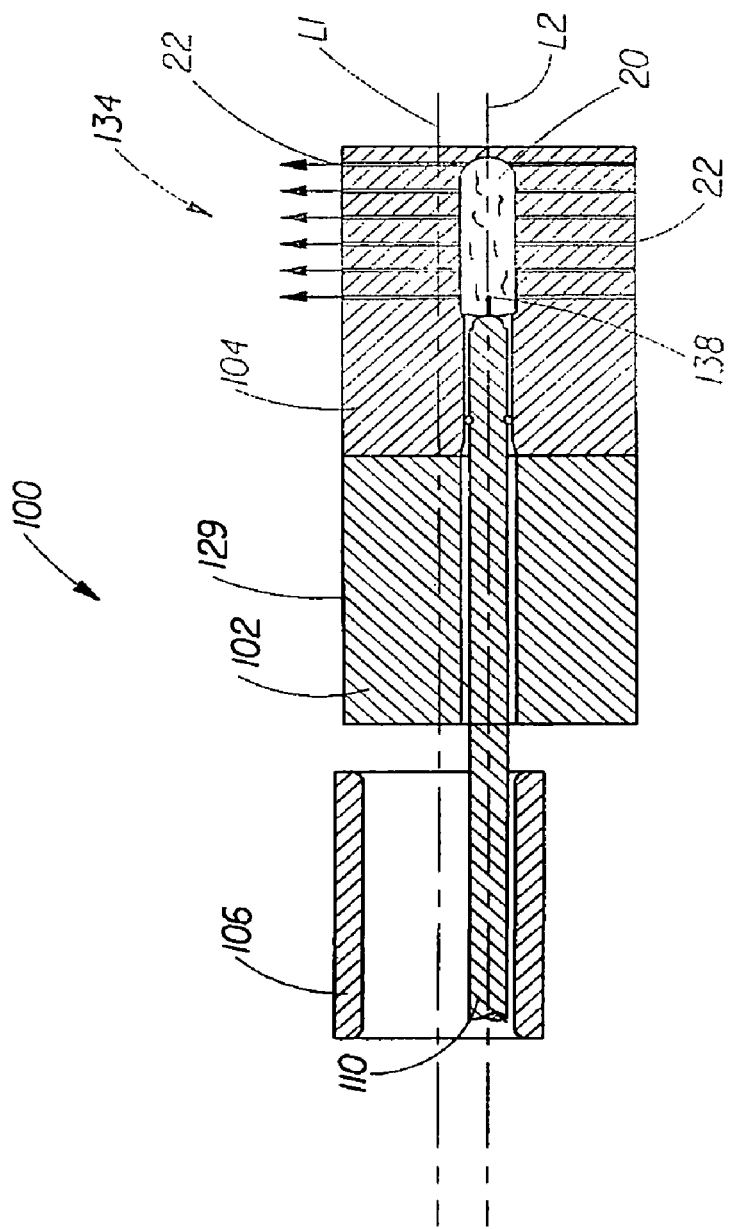
FIG. 21 is a cross-sectional view of an embodiment of the present invention showing a compressed pledget being subjected to a gas flow in the stabilization mold to form a stabilized product.

FIG. 21 is a cross-sectional view of an embodiment of the present invention showing compressed pledget 132 being subjected to a gas flow 134 provided through at least one pore 22 of the stabilization mold 104 to form a stabilized product 20. The transfer member 110 is aligned with the second longitudinal centerline L2 aligned with the closed position 129 of the stabilization mold 104. The process conditions suitable for stabilizing the compressed pledget, including materials, gases, temperature, humidity, time, and the like, are disclosed above. Specifically, with respect to the temperature of the stabilizing mold 104, it may maintain the stabilizing mold 104 at elevated temperature of about 50° C. to about 150° C., and in one embodiment at about 100° C. to about 130° C., to prevent condensation of a gas, for example, a steam, inside the stabilization mold 104. The desired temperature of the stabilization mold 104 can be provided by any suitable means including, but not limited to, electric cartridge heaters.

During the supplying of the gas flow 134, the gas flow 134 may be supplied through a pressurized side of the stabilization mold 104 and vented through a venting side of the stabilization mold into the atmosphere to provide a flow of the gas through the compressed pledget inside the stabilization mold. The gas flow and venting can range from about 0.5 s to about 5 s, or from about 0.5 s to about 1.5 s. Various heat treatments may be implemented to stabilize the compressed pledget, including steam treatment, microwave treatment, conductive heating, and others.

Figure 22:
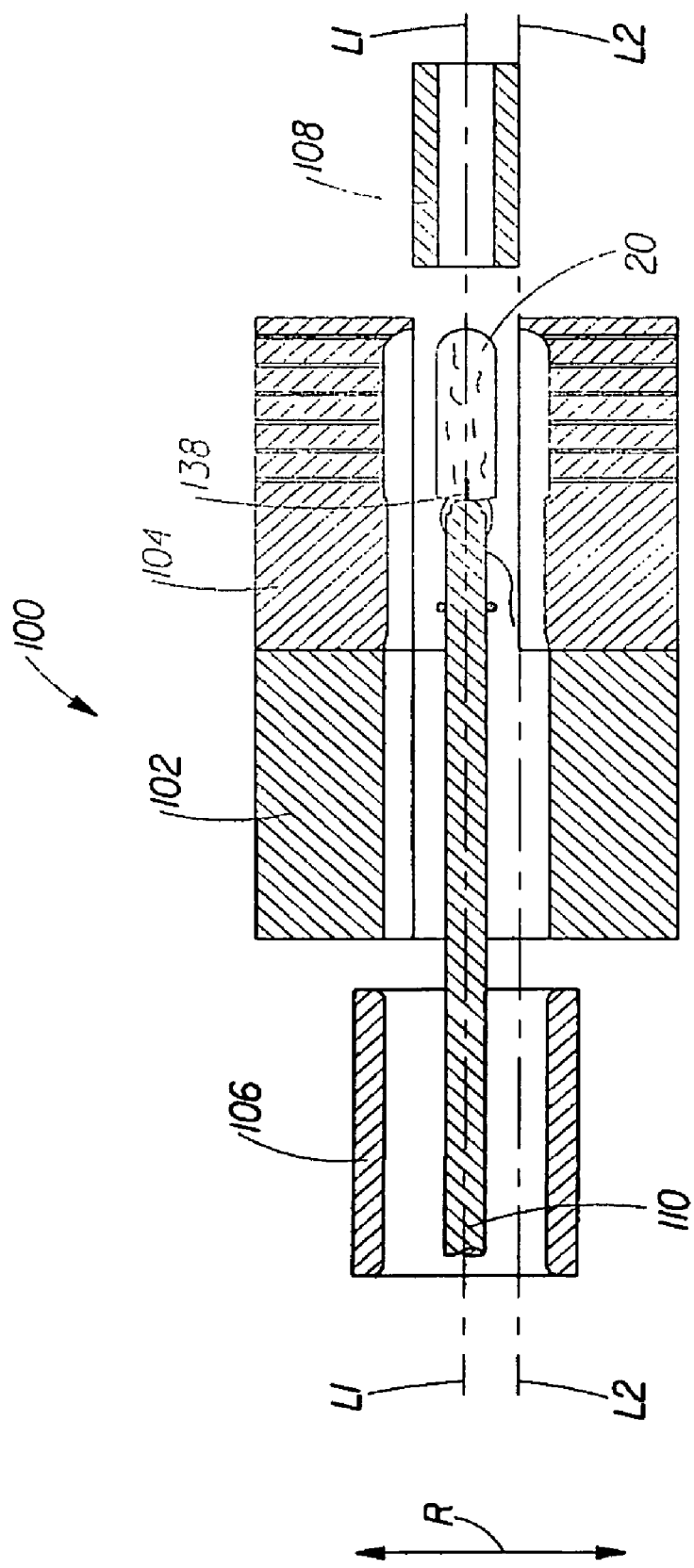
FIG. 22 is a cross-sectional view showing a stabilized product held by the transfer member inside the open stabilized mold.

FIG. 22 is a cross-sectional view of an embodiment of the present invention showing stabilized product 20 being stripped from the inner surface of the stabilization mold 104 and held by the needle(s) 138 of the transfer member 110 inside the stabilization mold 104 when the stabilization mold 104 is returned to the open position 128 (i.e., aligned with the first longitudinal centerline L1) and the transfer member 110 is returned to be aligned with the first longitudinal centerline L1.

As noted above, the transfer member 110 may include at least one needle 138 extending from the transfer member 110 longitudinally. The needle(s) 138 are capable of penetrating into the compressed pledget to enable a subsequent discharge of the stabilized product 20 from the stabilization mold 104. The number of needles 138 can include any suitable number of needles, and, for example, two or more needles may be provided to prevent turning of the tampon around a single needle around a longitudinal direction of the product 20.

The needle(s) 138 can have a relatively sharp point to provide penetration of the needle(s) 138 into the stabilized product 20 without damaging the stabilized product 20. The needle(s) 138 can be of any suitable diameter, for example, between about 1-2 mm, extending from the transfer member 110 at any suitable length sufficient to hold the stabilized product 20, for example, about 12 mm.

It should be noted that the above method of unloading stabilized products by the use of a transfer member having at least one needle can be applicable for unloading products, not only from a stabilization mold utilizing a gas flow, but also for any type of a stabilization mold, for example, utilizing conductive heating, microwave heating, and the like.

Figure 23:
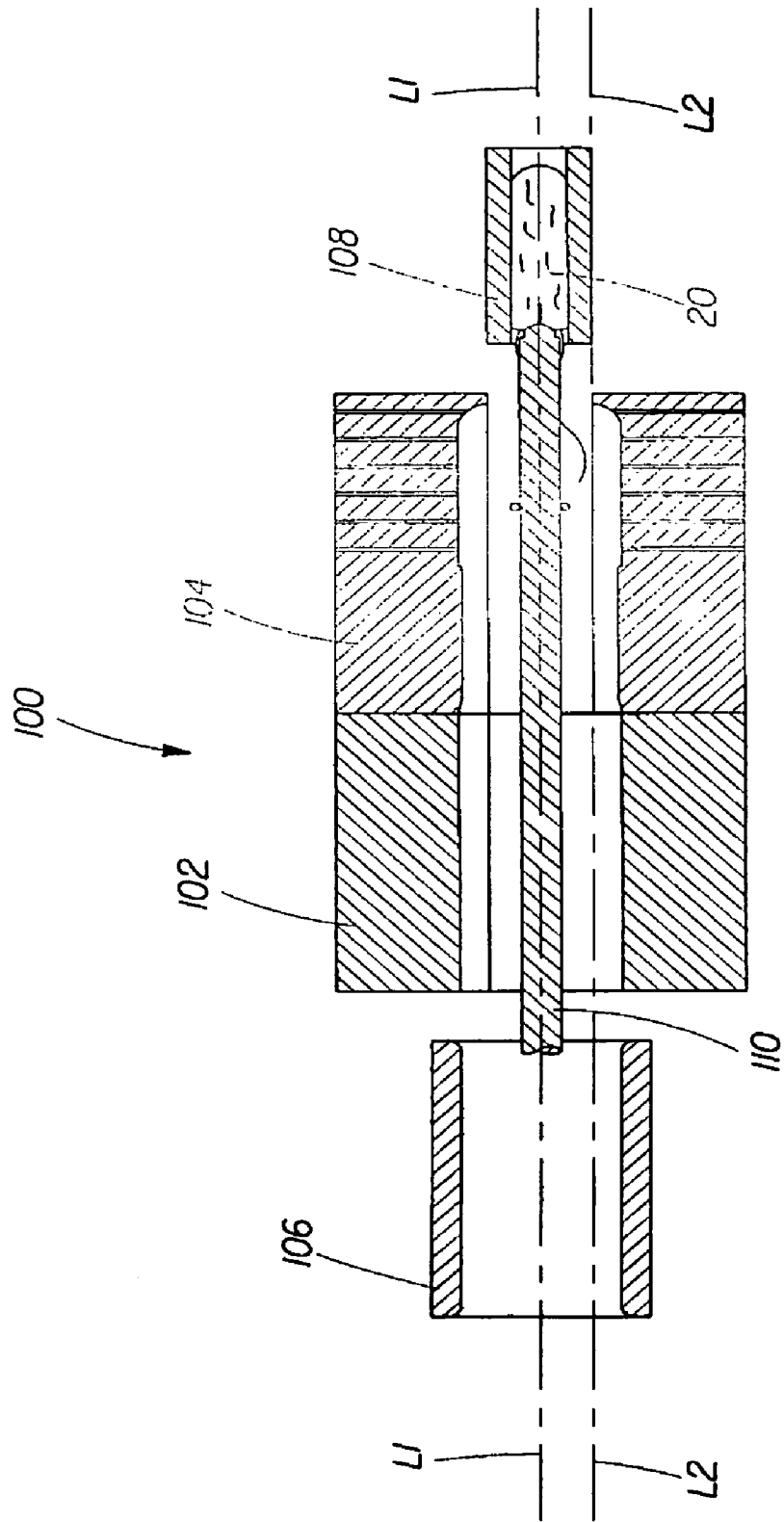
FIG. 23 is a cross-sectional view showing a stabilized product being loaded into a discharge carrier by the transfer member.

FIG. 23 is a cross-sectional view of an embodiment of the present invention showing stabilized product 20 being loaded into the product discharge carrier 108 by the transfer member 110. The transfer member 110 remains aligned with the first longitudinal centerline L1.

Figure 24:
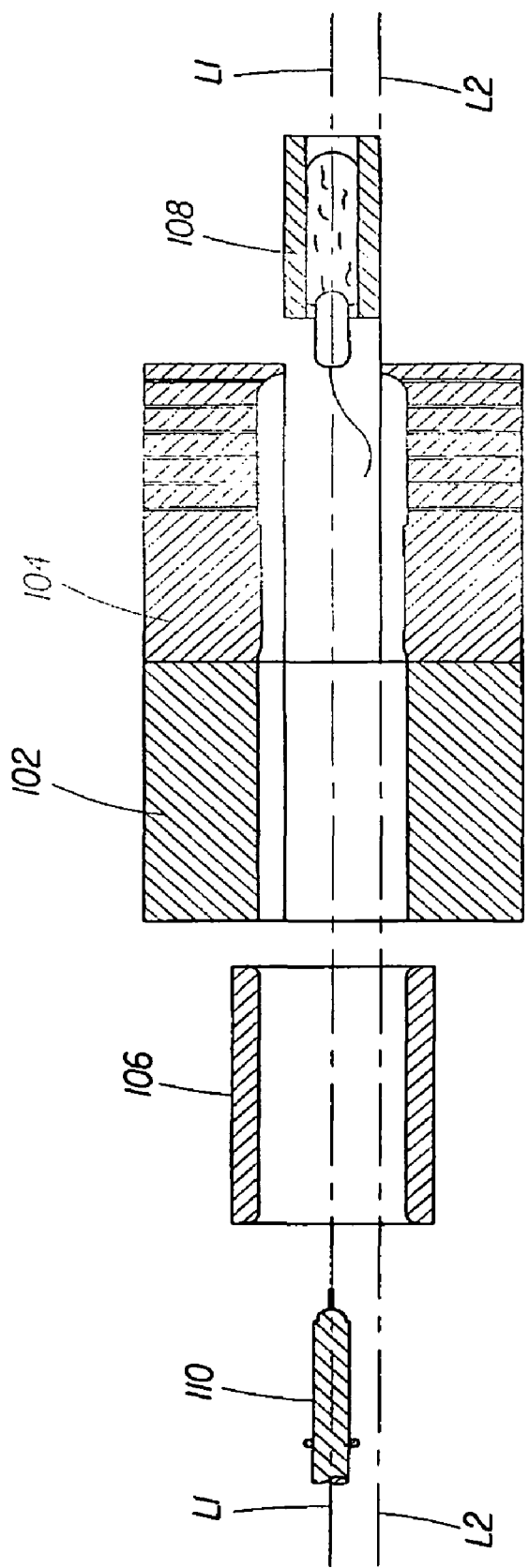
FIG. 24 is a cross-sectional view showing a transfer member retracted from the stabilized product.

FIG. 24 is a cross-sectional view of an embodiment of the present invention showing transfer member 110 being retracted from the stabilized product 20 and aligned with the first longitudinal centerline L1. The stabilized product 20 remains in the product discharge carrier 108 for further transferring to downstream processing, such as, for example, wrapping and packaging.

Measurement of expansion may be performed as follows, as described in U.S. Pat. No. 6,682,513.

Expansion Under Pressure Test:

This test is a modification of the standard syngyna test. The test may be used to determine the widthwise expansion under pressure of tampons made according to the present invention. Additionally, this test produces measurements of tampon width as a function of time from the start of the test. These measurements may be used to calculate a widthwise expansion rate by dividing the width at a given time interval minus the width at time zero by the total time elapsed in such time interval.

Figure 25:
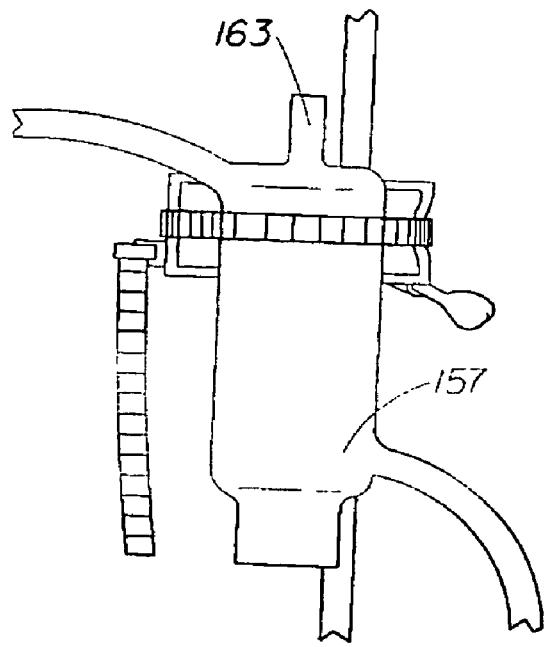
FIG. 25 is a front view of the syngyna test apparatus used to conduct the syngyna test, the expanded width test, and the widthwise expansion test described in this specification.
Figure 25A:
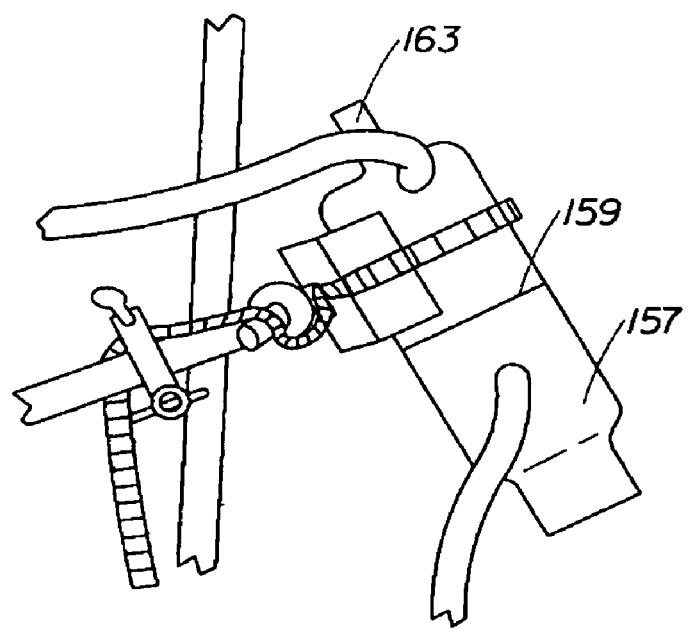
FIG. 25A is a side view of the apparatus shown in FIG. 25.

Procedures:

1. Use the following equipment.
   a) Ring stand
   b) Clamp, chain; VWR #21573-275
   c) Calibrated syngyna chamber
   d) Clamp, swivel; 21572-603 VWR
   e) Compressed air station with PSI gauge
   f) 40 inches of 6409-13 tubing (size 13; Tygon)
   g) Steel cylinder standards
   h) condoms, Calatex
   i) Steel cannula, peristaltic pump head and drive motor
   j) Beakers
   k) Traceable timer
   l) Rule
   m) 06429-18 tubing for air pressurizing of chamber ⅜" I.D.
   n) Tubing clamp
   o) Digital camera
   p) Leveling protractor
   q) KLC 9-25-00 not needed
2. Set up equipment as pictured in FIG. 25.
3. Setup tripod and camera in front of syngyna chamber 157. Place camera as close to the chamber as possible while still being able to see the entire chamber in the view finder.
4. Adjust angle of chamber to 30° from upright (60° on protractor), as shown in FIG. 25A.
5. Adjust angle of camera to 30° so that it is parallel to the chamber. Looking through view-finder, the calibration line 159 should be even and solid.
6. Assemble pump head and motor; insert tubing; insert cannula into tubing.

7. Insert a condom into the syngyna chamber, cut off tip and secure top and bottom around ends of chamber with rubber bands. (Same procedure as in syngyna method). Place small rule inside chamber in front of condom, then secure bottom of condom around opening of chamber.

8. Turn on pump motor and dispense test fluid (sheep's blood, defibrinated) for a set period of time into a tared beaker. Weigh beaker and determine flow rate. Target is 1 gram per minute.

9. Insert tampon into chamber, centering it using calibration line 159.

10. Close clamp on air tube and turn on air pressure. Adjust to 0.5 psi.

11. Insert cannula into top of chamber 163. Be sure it touches top of tampon.

12. Check angle of chamber again. Check set-up by looking through viewfinder of camera. Be sure everything is straight and level. Be sure timer is visible in frame.

13. Take a picture of dry tampon in chamber. This will be time=0.

14. Start pump and timer simultaneously.

15. Take a picture of tampon each minute until it leaks.

16. At leak point, release pressure in chamber and remove tampon.

17. Download images to computer.

18. Using ScionImage analysis software, open each image and measure at least one or two rules. That is, use the measurement line to draw a line over a certain number of millimeters on the rule in an image. Then select "Analyze" on menu bar, then "set scale." Type in number of millimeters measured in image. The software will then set a pixels per-millimeter scale.

19. Using the same measurement line tool, measure the tampon in the image. Measure the widest portion of the tampon as well as the width at the top and bottom of the tampon. For purposes of this instruction, the "top" of the tampon to the widest part above the calibration line on the chamber. The "bottom" is approximate—by 7 mm from the bottom most edge of the tampon.

20. Record measurements.

21. Verification measurements can be made on known standards such as cylinders.

22. Special notes: Periodically check angle of camera and be sure set-up is not disturbed. Check angle of chamber after insertion of each tampon. While it is not necessary to set scale for each image, it is recommended to do so frequently. It is recommended to check scale by measuring rule in image at least every two images.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for stabilizing a product from a pledget, comprising the steps of:
   providing a pledget into a compression mold;
   compressing said pledget in said compression mold to form a compressed pledget;
   unloading said compressed pledget from said compression mold and loading said compressed pledget into a stabilization mold by a transfer member, whereby said transfer member advances to a loading position;
   retracting said transfer member to a stabilizing position;
   stabilizing said compressed pledget in said stabilization mold to form a stabilized product, wherein said transfer member remains in said stabilizing position during at least a portion of the step of stabilizing said compressed pledget; and
   unloading said stabilized product from said stabilization mold.

2. The process according to claim 1, wherein said transfer member engages a proximal end of said compressed pledget and said transfer member remains engaged with said proximal end in both said loading position and said stabilizing position.

3. The process according to claim 2, wherein said proximal end expands during the step of retracting said transfer member.

4. The process according to claim 3, wherein said transfer member in said stabilizing position contains said proximal end of the compressed pledget inside said stabilization mold during the step of stabilizing said compressed pledget.

5. The process according to claim 1, wherein said transfer member contacts either an insertion end or a withdrawal end of said stabilized product.

6. The process of claim 5, wherein said stabilized product is a tampon.

7. The process according to claim 1, wherein said compressed pledget has a proximal end and a distal end, said distal end of said compressed pledget substantially fills said closed distal end of said stabilization mold when said transfer member is in said loading position.

8. The process according to claim 7, wherein said distal end of said compressed pledget has a first density when said transfer member is in said loading position and said proximal end of said compressed pledget has a second density when said transfer member is in said loading position, wherein said second density is greater than said first density.

9. The process according to claim 8, wherein said distal end of said compressed pledget substantially fills said closed distal end of said stabilization mold when said transfer member is in said stabilizing position.

10. The process according to claim 9, wherein said transfer member remains engaged with said proximal end of said compressed pledget in said stabilizing position.

11. The process according to claim 10, wherein said distal end of said compressed pledget substantially maintains said first density when said transfer member is in said stabilizing position and said proximal end of said compressed pledget has said first density when said transfer member is in said stabilizing position.

12. The process according to claim 9, wherein said compressed pledget has substantially uniform density from said proximal end to said distal end prior to the step of stabilizing said compressed pledget.

13. The process according to claim 1, wherein said compressed pledget has a proximal end and a distal end, said process further comprising the step of selecting said loading position to correspond to a desired density created in said distal end of said compressed pledget when said transfer member is in said loading position.

14. The process according to claim 13, further comprising the step of selecting said stabilizing position to correspond to said desired density created in said proximal end of said compressed pledget when said transfer member is in said stabilizing position.

* * * * *